(12) United States Patent
Wender et al.

(10) Patent No.: US 7,151,116 B2
(45) Date of Patent: Dec. 19, 2006

(54) APOPTOLIDIN ANALOGS AND DERIVATIVES FOR INDUCING APOPTOSIS IN TRANSFORMED CELLS

(75) Inventors: Paul A. Wender, Menlo Park, CA (US); Orion D. Jankowski, Burlingame, CA (US); Elie A. Tabet, Durham, NC (US)

(73) Assignee: Board of Trustees of The Leland Stanford Junior University, Stanford, CA (US)

( * ) Notice: Subject to any disclaimer, the term of this patent is extended or adjusted under 35 U.S.C. 154(b) by 20 days.

(21) Appl. No.: 10/757,810

(22) Filed: Jan. 13, 2004

(65) Prior Publication Data

US 2004/0180841 A1 Sep. 16, 2004

Related U.S. Application Data

(60) Provisional application No. 60/472,657, filed on May 21, 2003, provisional application No. 60/439,954, filed on Jan. 13, 2003.

(51) Int. Cl.
*A61K 31/35* (2006.01)

(52) U.S. Cl. .................. 514/450; 549/271; 548/431

(58) Field of Classification Search ............... 549/271; 548/431; 514/450
See application file for complete search history.

(56) References Cited

U.S. PATENT DOCUMENTS

| | | | | |
|---|---|---|---|---|
| 5,962,290 A | | 10/1999 | Khosla et al. | ............... 435/183 |
| 6,548,485 B1 | * | 4/2003 | Khosla et al. | ................. 514/28 |
| 2002/0049168 A1 | | 4/2002 | Khosla et al. | ................. 514/28 |
| 2002/0077300 A1 | | 6/2002 | Khosla et al. | ................. 514/23 |

OTHER PUBLICATIONS

Salmon et al, Understanding and exploiting the mechanistic basis for selectivity of polyketide inhibitors of F0F1-ATPase, PNAS, 97(26), pp. 14766-14771, Dec. 19, 2000.*

Hayakawa, et al., "Structure of apoptolidin, a specific apoptosis inducer in transformed cells," J. Am. Chem. Soc. (1998) 120:3524-3525.

Pennington, et al., "Toward a stable apoptolidin derivative: identification of isoapoptolidin and selective deglycosylation of apoptolidin," Org. Lett. (2002) 4:3823-3825.

Salomon, et al., "Apoptolidin, a selective cytotoxic agent, is an inhibitor of $F_0F_1$-ATPase," Chem. Biol. (2000) 54:1-10.

Salomon, et al., "Structure-activity relationships within a family of selectively cytotoxic macrolide natural products," Org. Lett. (2001) 3:57-59.

Salomon, et al., "Understanding and exploiting the mechanistic basis for selectivity of polyketide inhibitors of $F_0F_1$-ATPase," Proc. Natl. Acad. Sci.USA (2000) 97:14766-14771.

Wender, et al., "Isoapoptolidin: structure and activity of the ring-expanded isomer of apoptolidin," Org. Lett. (2002) 4:3819-3822.

Wender, et al., "Toward a structure-activity relationship for apoptolidin: selective functionalization of the hydroxyl group array," Org. Lett. (2003) 5:487-490.

Wender, et al., "Facile synthesis access to and biological evaluation of the macrocyclic core of apoptolidin," Org. Lett. (2003) 5:2299-2302.

* cited by examiner

*Primary Examiner*—Amelia A. Owens
(74) *Attorney, Agent, or Firm*—Mintz, Levin, Cohn, Ferris, Glovsky and Popeo, P.C.

(57) ABSTRACT

The invention provides novel apoptosis-inducing compounds that include isolated, purified isoapoptolidin, and selectively functionalized isoapoptolidin derivatives and stereoisomers thereof; selectively functionalized apoptolidin derivatives and stereoisomers thereof; and deglycosylated isoapoptolidin and selectively functionalized derivatives and stereoisomers thereof. The isoapoptolidin, apoptolidin, and deglycosylated isoapoptolidin derivatives may be functionalized by substituting any or all of the methoxyl or hydroxyl groups of the parent molecule. Pharmaceutical compositions and methods for using the compounds are also provided.

56 Claims, 3 Drawing Sheets

APOPTOLIDIN ANALOGS AND DERIVATIVES FOR INDUCING APOPTOSIS IN TRANSFORMED CELLS

CROSS-REFERENCE TO RELATED APPLICATIONS

This application claims priority under 35 U.S.C. § 119(e)(1) to provisional U.S. patent applications Ser. No. 60/439,954, filed Jan. 13, 2003, and 60/472,657, filed May 21, 2003.

GOVERNMENT RIGHTS

This invention was made with United States Government support under contract CA31845 awarded by the National Cancer Institute. The United States Government has certain rights in this invention.

TECHNICAL FIELD

This invention relates generally to apoptolidin, and more particularly relates to novel apoptolidin analogs and derivatives that are effective in inducing apoptosis in transformed cells. The invention also pertains to pharmaceutical compositions and methods for treating a patient in need of anti-cancer therapy or therapy for the treatment of other disorders that are responsive to selective apoptosis, also known as programmed cell death.

BACKGROUND

Apoptolidin is a 20-membered macrolide that selectively induces apoptosis in certain cancer cell lines. Apoptosis is an important mechanism in the treatment of cancer and consequently, agents that can selectively induce apoptosis in cancer cells have great therapeutic use. The success of apoptolidin as a potentially powerful anti-cancer agent is demonstrated by the molecule's status as among the top 0.1% most selective cytotoxic agents of 37,000 compounds tested by the National Cancer Institute on 60 human cancer cell lines (NCI 60).

Apoptolidin

Apoptolidin was first isolated by Seto et al., who, in 1997, found that apoptolidin, isolated from *Nocardiopsis* sp. was capable of inducing apoptosis in rat glial cells transformed with the adenovirus E1A or E1A/E1B19K/E1B54K oncogenes but that the macrolide had no cytotoxic effect on untransformed rat glial cells or on normal fibroblasts. Kim et al. (1997) *J. Antibiot.*, 50:628–630; Kim et al. (1998) *J. Am. Chem. Soc.*, 120:3524–3525. It has been hypothesized that the cell death induced by apoptolidin results from the macrolide's ability to inhibit oxidative phosphorylation by targeting mitochondrial $F_0F_1$-ATP synthetase. Salomon et al. (2000) *Proc. Natl. Acad. Sci.*, 97(26):14766–14771; Salomon et al. (2000) *Chem. & Biol.*, 54:1–10. The ability of apoptolidin to inhibit eukaryotic mitochondrial ATP synthetase places this molecule in a growing family of structurally related macrolide antibiotics including the anti-fungal agents oligomycin and ossamycin.

While apoptolidin has been found to be an effective apoptosis-inducing agent in some cancer cell lines, its effectiveness is not universal. Salomon et al. have presented experiments that suggest that macrolide inhibitors of mitochondrial $F_0F_1$-ATP synthetase ($F_0F_1$-ATPase) selectively kill metabolically active tumor cells that do not exhibit a high level of anaerobic carbon metabolism in the presence of oxygen (a phenomenon known as the Warburg effect). For those cell lines that exhibit the Warburg effect, it has been demonstrated that treatment of the tumor cell lines with the lactase dehydrogenase inhibitor oxamate and the Embden-Meyerhof pathway inhibitor 2-deoxyglucose sensitizes the tumor cells to apoptolidin treatment. Salomon et al., *PNAS*, supra. Salomon et al. have hypothesized that these two inhibitors modulate apoptolidin activity by channeling carbon flux into the mitochondria and consequently, initiate mitochondrially derived aerobic energy. The foregoing finding, however, does not explain apoptolidin's selectivity against different cell lines.

Accordingly, there is a need in the art to determine the structure-activity relationship of apoptolidin in order to

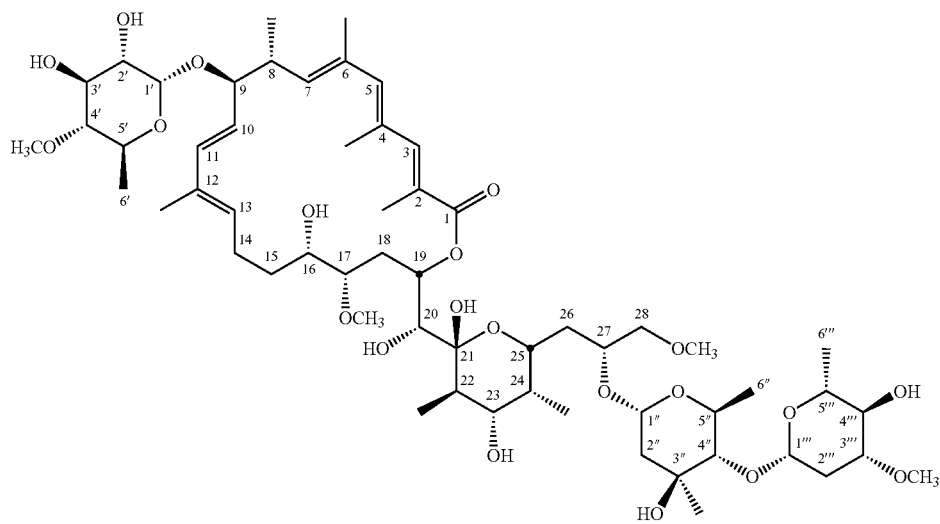

obtain information on the reasons for the cell-line specificity of this important molecule in its natural state and, consequently, be able to prepare analogs and derivatives of apoptolidin, including compounds that are broadly active as well as those that are cell-line specific (and thereby target specific types of abnormal or diseased cells). Through the preparation of such analogs and derivatives, therapeutic anti-cancer agents may be prepared using apoptolidin analogs and derivatives.

The present invention is the result of extensive, systematic research into apoptolidin analogs, including isolated and purified isomers of apoptolidin, and apoptolidin derivatives, prepared through modification of the functional groups of the apoptolidin molecule. To the best of the inventors' knowledge, the compounds, compositions, and methods of the invention are completely unknown and completely unsuggested by the art.

SUMMARY OF THE INVENTION

The present invention is directed to the aforementioned need in the art, and provides novel compounds that induce apoptosis in cancerous cells but not in normal cells. The compounds are apoptolidin analogs and derivatives thereof, including an apoptolidin isomer, "isoapoptolidin," as well as functionalized isoapoptolidin, functionalized apoptolidin, "truncated" (deglycosylated) isoapoptolidin, and functionalized "truncated" (deglycosylated) isoapoptolidin.

In a first embodiment, the invention provides isolated, purified isoapoptolidin as a new composition of matter. Isoapoptolidin is a ring-expanded macrolide isomer of apoptolidin, and has the structure of formula (I)

(a) $C_1$–$C_{24}$ hydrocarbyloxy, optionally substituted with one or more halogen atoms, e.g., $C_1$–$C_{24}$ alkoxy (—O—($C_1$–$C_{24}$ alkyl)), $C_6$–$C_{24}$ aralkoxy (—O—($C_6$–$C_{24}$ aralkyl)), $C_6$–$C_{24}$ alkaryloxy (—O—($C_6$–$C_{24}$ alkaryl)), $C_1$–$C_{24}$ haloalkoxy (—O—($C_1$–$C_{24}$ haloalkyl)), and $C_6$–$C_{24}$ haloaralkoxy (—O—($C_6$–$C_{24}$ haloaralkyl);

(b) $C_2$–$C_{25}$ acyloxy (—O—(CO)—($C_1$–$C_{24}$ hydrocarbyl)), e.g., —O—(CO)—($C_1$–$C_{24}$ alkyl), —O—(CO)—($C_5$–$C_{24}$ aryl), —O—(CO)—($C_6$–$C_{24}$ aralkyl), and —O—(CO)—($C_6$–$C_{24}$ alkaryl));

(c) $C_2$–$C_{25}$ haloacyloxy (—O—(CO)—($C_2$–$C_{24}$ halohydrocarbyl)), e.g., —O—(CO)—($C_1$–$C_{24}$ haloalkyl), —O—(CO)—($C_5$–$C_{24}$ haloaryl), —O—(CO)—($C_5$–$C_{24}$ haloaralkyl), and —O—(CO)—($C_5$–$C_{24}$ haloalkaryl);

(d) $C_2$–$C_{25}$ thioacyloxy (—O—(CS)—($C_2$–$C_{24}$ hydrocarbyl)), e.g., —O—(CS)—($C_1$–$C_{24}$ alkyl), —O—(CS)—($C_5$–$C_{24}$ aryl), —O—(CS)—($C_5$–$C_{24}$ aralkyl), and —O—(CS)—($C_5$–$C_{24}$ alkaryl);

(e) $C_2$–$C_{25}$ thiohaloacyloxy (—O—(CS)—($C_2$–$C_{24}$ hydrocarbyl)), e.g., —O—(CS)—($C_1$–$C_{24}$ haloalkyl), —O—(CS)—($C_5$–$C_{24}$ haloaryl), —O—(CS)—($C_5$–$C_{24}$ haloaralkyl), and —O—(CS)—($C_5$–$C_{24}$ haloalkaryl), (f) $C_2$–$C_{25}$ carbonato (—O—(CO)—O—($C_1$–$C_{24}$ hydrocarbyl)), e.g., $C_2$–$C_{25}$ alkylcarbonato (—O—(CO)—O—($C_1$–$C_{24}$ alkyl)), $C_6$–$C_{25}$ arylcarbonato (—O—(CO)—O—($C_5$–$C_{24}$ aryl)), $C_6$–$C_{25}$ aralkylcarbonato (—O—(CO)—O—($C_5$–$C_{24}$ aralkyl)), and $C_6$–$C_{25}$ alkarylcarbonato (—O—(CO)—O—($C_5$–$C_{24}$ alkaryl));

(g) halogenated $C_2$–$C_{25}$ carbonato (—O—(CO)—O—($C_1$–$C_{24}$ halohydrocarbyl)), e.g., $C_2$–$C_{25}$ haloalkylcarbonato

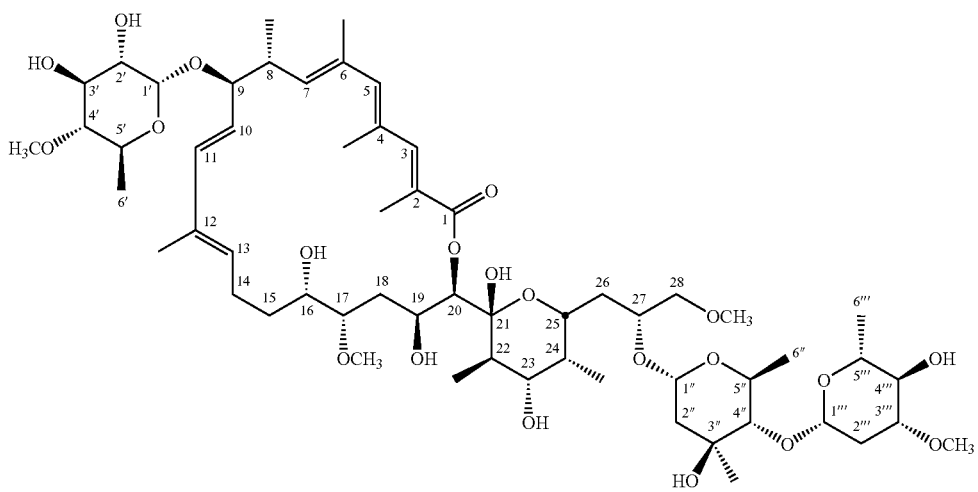

Isoapoptolidin

The compounds of the invention also include functionalized isoapoptolidin, functionalized apoptolidin, functionalized deglycosylated isoapoptolidin, deglycosylated isoapoptolidin, and stereoisomers thereof. The functionalized compounds have the structure of isoapoptolidin, apoptolidin, and deglycosylated isoapoptolidin, respectively, wherein at least one hydroxyl group within the molecule is replaced with a substituent selected from:

(—O—(CO)—O—($C_1$–$C_{24}$ haloalkyl)), $C_6$–$C_{25}$ haloarylcarbonato (—O—(CO)—O—($C_5$–$C_{24}$ haloaryl)), $C_6$–$C_{25}$ haloaralkylcarbonato (—O—(CO)—O—($C_5$–$C_{24}$ haloaralkyl)), and $C_6$–$C_{25}$ haloalkarylcarbonato (—O—(CO)—O—($C_5$–$C_{24}$ haloalkaryl));

(h) $C_2$–$C_{25}$ thiocarbonato (—O—(CS)—O—($C_1$–$C_{24}$ hydrocarbyl)), e.g., $C_2$–$C_{25}$ alkylcarbonato (—O—(CS)—O—($C_1$–$C_{24}$ alkyl)), $C_6$–$C_{25}$ arylcarbonato (—O—(CS)—O—($C_5$–$C_{24}$ aryl)), $C_6$–$C_{25}$ aralkylcarbonato (—O—(CS)—O—($C_5$–$C_{24}$ aralkyl)), and $C_6$–$C_{25}$ alkarylcarbonato (—O—(CS)—O—($C_5$–$C_{24}$ alkaryl));

(i) halogenated $C_2$–$C_{25}$ thiocarbonato (—O—(CS)—O—($C_1$–$C_{24}$ halohydrocarbyl)), e.g., $C_2$–$C_{25}$ haloalkylthiocarbonato (—O—(CS)—O—($C_1$–$C_{24}$ haloalkyl)), $C_6$–$C_{25}$ haloarylthiocarbonato (—O—(CS)—O—($C_5$–$C_{24}$ haloaryl)), $C_6$–$C_{25}$ haloaralkylthiocarbonato (—O—(CS)—O—($C_5$–$C_{24}$ haloaralkyl)), and $C_6$–$C_{25}$ haloalkarylthiocarbonato (—O—(CS)—O—($C_5$–$C_{24}$ haloalkaryl));

(j) carbamoyloxy (—O—(CO)—$NH_2$), mono-($C_1$–$C_{24}$ alkyl)-substituted carbamoyloxy (—O—(CO)—NH($C_1$–$C_{24}$ alkyl)), di-($C_1$–$C_{24}$ alkyl)-substituted carbamoyloxy (—O—(CO)—N($C_1$–$C_{24}$ alkyl)$_2$), mono-($C_6$–$C_{24}$ aryl)-substituted carbamoyloxy (—O—(CO)—NH-aryl), di-($C_6$–$C_{24}$ aryl)-substituted carbamoyloxy (—O—(CO)—N(aryl)$_2$), and di-N—($C_1$–$C_{24}$ alkyl), N—($C_6$–$C_{24}$ aryl)-substituted carbamoyloxy;

(k) thiocarbamoyloxy (—O—(CS)—$NH_2$), mono-($C_1$–$C_{24}$ alkyl)-substituted thiocarbamoyloxy (—O—(CS)—NH($C_1$–$C_{24}$ alkyl)), di-($C_1$–$C_{24}$ alkyl)-substituted thiocarbamoyloxy (—O—(CS)—N($C_1$–$C_{24}$ alkyl)$_2$), mono-($C_6$–$C_{24}$ aryl)-substituted thiocarbamoyloxy (—O—(CS)—NH-aryl), di-($C_6$–$C_{24}$ aryl)-substituted carbamoyloxy (—O—(CS)—N(aryl)$_2$), and di-N—($C_1$–$C_{24}$ alkyl), N—($C_6$–$C_{24}$ aryl)-substituted thiocarbamoyloxy;

(l) sulfamoyloxy (—O—$SO_2$—$NH_2$), mono-($C_1$–$C_{24}$ alkyl)-substituted sulfamoyloxy (—O—$SO_2$—NH($C_1$–$C_{24}$ alkyl)), di-($C_1$–$C_{24}$ alkyl)-substituted sulfamoyloxy (—O—$SO_2$—N($C_1$–$C_{24}$ alkyl)$_2$), mono-($C_6$–$C_{24}$ aryl)-substituted sulfamoyloxy (—O—$SO_2$—NH-aryl), di-($C_6$–$C_{24}$ aryl)-substituted sulfamoyloxy (—O—$SO_2$—N(aryl)$_2$), and di-N—($C_1$–$C_{24}$ alkyl), N—($C_6$–$C_{24}$ aryl)-substituted sulfamoyloxy; and (m) protected hydroxyl groups such as tri-($C_1$–$C_{12}$ hydrocarbyl)-substituted silyloxy and substituted methyl ethers.

The functionalized compounds of the invention also encompass other isoapoptolidin, apoptolidin, and deglycosylated isoapoptolidin analogs in which the core compounds have been modified so that: (a) a double bond is converted to a single bond via catalytic hydrogenation or nucleophilic addition; (b) a 1,3-diene functionality is converted to a cyclic group by a Diels-Alder reaction with a dienophile; and/or (c) a 1,2-diol functionality has been converted to a cyclic ether by reaction with a suitable reagent. The compounds of the invention may be functionalized to contain any or all of the modifications (a), (b), or (c), in addition to or in lieu of the hydroxyl group substitutions enumerated above.

In one preferred embodiment, a functionalized isoapoptolidin compound is provided having the structure of formula (II)

(II)

or is a stereoisomer thereof, wherein $Q^1$, $Q^2$, $Q^3$, $Q^4$, $Q^5$, $Q^6$, $Q^7$, and $Q^8$ are selected from H, $C_1$–$C_{12}$ hydrocarbyl, acyl of the formula —(CO)—$R^5$ wherein $R^5$ is $C_1$–$C_{12}$ hydrocarbyl, and hydroxyl-protecting groups, and $R^1$, $R^2$, $R^3$, and $R^4$ are independently selected from $C_1$–$C_{12}$ alkyl and H.

In another preferred embodiment of the invention, a functionalized apoptolidin compound is provided having the structure of formula (III)

or is a stereoisomer thereof, wherein $Q^1$, $Q^2$, $Q^4$, $Q^5$, $Q^6$, $Q^8$, and $Q^9$ are independently selected from H, $C_1$–$C_{12}$ hydrocarbyl, acyl of the formula —(CO)—$R^5$, and hydroxyl-protecting groups, and $R^1$, $R^2$, and $R^3$ are independently selected from $C_1$–$C_{12}$ alkyl and H.

In yet another embodiment, the invention encompasses pharmaceutical compositions containing a therapeutically effective amount of an apoptolidin analog or derivative as

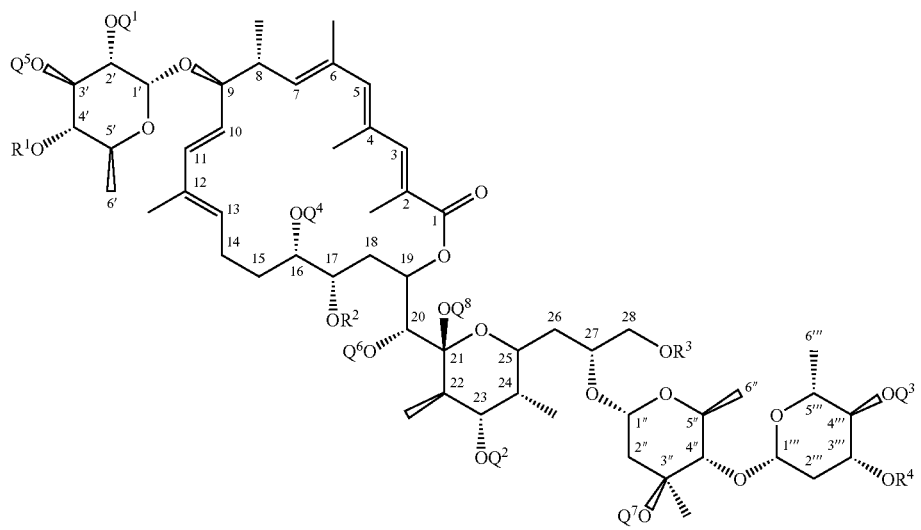

(III)

or is a stereoisomer thereof, wherein $Q^1$, $Q^2$, $Q^3$, $Q^4$, $Q^5$, $Q^6$, $Q^7$, $Q^8$, $R^1$, $R^2$, $R^3$, and $R^4$ are defined as for the functionalized isoapoptolidin compounds of formula (II), with the proviso that at least one of $Q^1$, $Q^2$, $Q^3$, $Q^4$, $Q^5$, $Q^6$, $Q^7$, and $Q^8$ is other than H when $R^1$, $R^2$, $R^3$, and $R^4$ are methyl and the compound has the stereoisomeric configuration of formula (III).

In a further preferred embodiment, a functionalized deglycosylated isoapoptolidin compound is provided having the structure of formula (IV)

provided herein in combination with a pharmaceutically acceptable carrier. The compositions are generally "unit dosage" forms in which the therapeutically effective amount is suitable for a single dosage. The compositions may be immediate release or controlled release, and, if controlled release, are preferably sustained release. For those compounds that are orally active, oral dosage forms are preferred, in which case the carrier is one that is suitable for oral ingestion.

(IV)

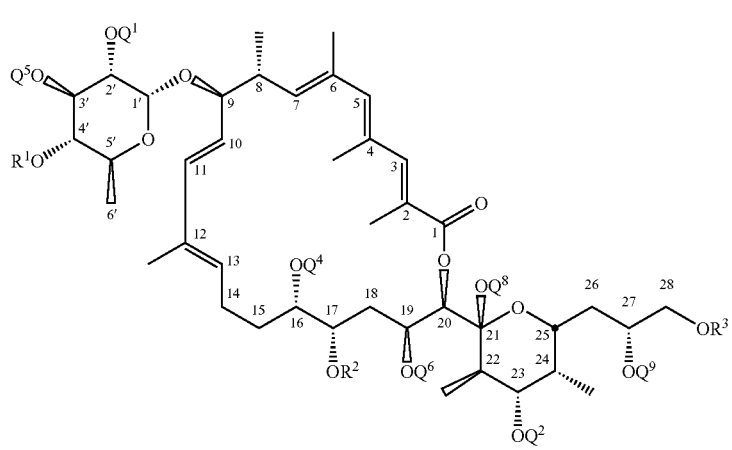

The invention also provides a method for treating a mammalian patient in need of anti-cancer treatment by administering a therapeutically effective amount of an apoptolidin analog or derivative as provided herein. Generally, the analog or derivative is administered in a pharmaceutical composition as described above.

DETAILED DESCRIPTION OF THE PREFERRED EMBODIMENTS

I. Definitions and Nomenclature

Figure 1:
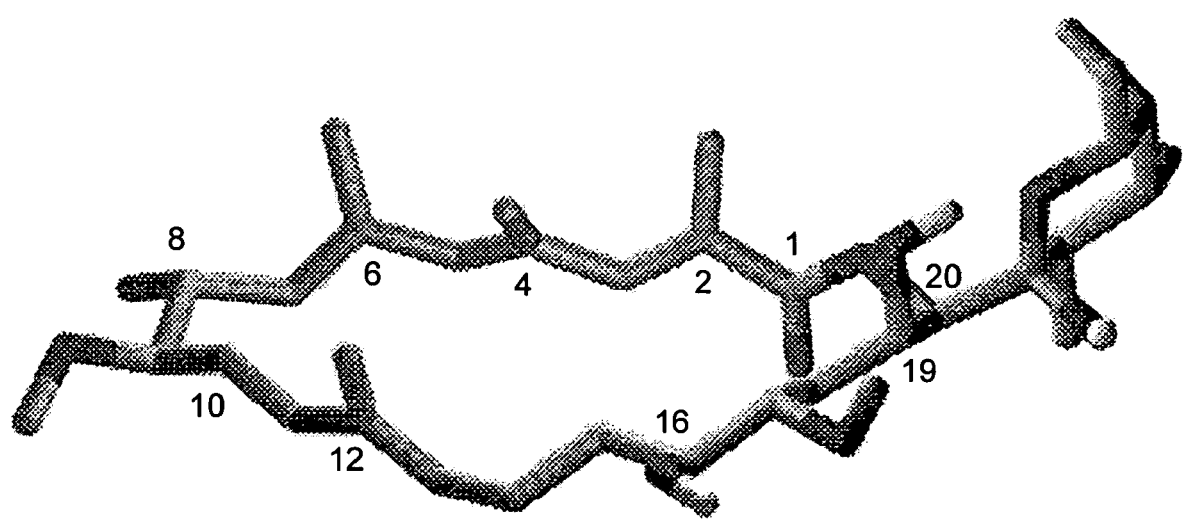
FIG. 1 shows a representative solution conformation of deglycosylated isoapoptolidin in the region from C-1 to C-26.

Unless otherwise indicated, the invention is not limited to specific synthetic methods, analogs, substituents, pharmaceutical formulations, formulation components, modes of administration, or the like, as such may vary. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Thus, for example, reference to "a substituent" includes a single substituent as well as two or more substituents that may be the same or different, reference to "a compound" encompasses a combination or mixture of different compounds as well as a single compound, reference to "a pharmaceutically acceptable carrier" includes two or more such carriers as well as a single carrier, and the like.

In this specification and in the claims that follow, reference will be made to a number of terms, which shall be defined to have the following meanings:

The term "isomer" is used to describer a chemical compounds having the same number and kind of atoms (and hence the same molecular weight) as a parent compound but differing in the arrangement or configuration of the atoms. The term "stereoisomer" refers to chemical compounds that have identical atomic constituents but differ in the spatial arrangement of the atoms.

The term "analog" is used to describe a structural derivative of a parent compound that often differs from it by a single element. As used herein, the term analog includes isomers of a parent compound, e.g., isoapoptolidin is an analog as well as an isomer of apoptolidin.

As used herein, the term "derivative" is used to mean a compound derived or obtained from another and containing essential elements of the parent substance, e.g., the functionalized apoptolidin compounds of the invention are derivatives of apoptolidin, and the functionalized isoapoptolidin compounds of the invention are derivatives of isoapoptolidin.

As used herein, the phrase "having the formula" or "having the structure" is not intended to be limiting and is used in the same way that the term "comprising" is commonly used.

The term "alkyl" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl, and the like. Generally, although again not necessarily, alkyl groups herein contain 1 to about 12 carbon atoms. The term "lower alkyl" intends an alkyl group of 1 to 6 carbon atoms. Preferred lower alkyl substituents contain 1 to 4 carbon atoms, and particularly preferred such substituents contain 1 or 2 carbon atoms (i.e., methyl and ethyl). "Substituted alkyl" refers to alkyl substituted with one or more substituent groups, and the terms "heteroatom-containing alkyl" and "heteroalkyl" refer to alkyl in which at least one carbon atom is replaced with a heteroatom, as described in further detail infra. If not otherwise indicated, the term "alkyl" includes linear, branched, cyclic, unsubstituted, substituted, and/or heteroatom-containing alkyl.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 24 carbon atoms, and particularly preferred aryl groups contain 5 to 12 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to an aryl substituent in which at least one carbon atom is replaced with a heteroatom, as will be described in further detail infra. If not otherwise indicated, the term "aryl" includes unsubstituted, substituted, and/or heteroatom-containing aromatic substituents.

The term "aralkyl" refers to an alkyl group with an aryl substituent, and the term "alkaryl" refers to an aryl group with an alkyl substituent, wherein "alkyl" and "aryl" are as defined above. In general, aralkyl and alkaryl groups herein contain 6 to 25 carbon atoms, while preferred aralkyl and alkaryl groups contain 6 to 13 carbon atoms. Examples of aralkyl groups include, without limitation, benzyl, 2-phenylethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-dienyl, and the like.

When a functional group is termed "protected," this means that the group is in modified form to preclude undesired side reactions at the protected site. Suitable protecting groups for the compounds of the present invention will be recognized from the present application taking into account the level of skill in the art, and with reference to standard textbooks, such as Greene et al., *Protective Groups in Organic Synthesis* (New York: Wiley, 1991).

The term "hydrocarbyl" refers to univalent moieties composed of hydrogen and carbon and containing 1 to about 24 carbon atoms, preferably about 1 to 12 carbon atoms, including linear, branched, cyclic, saturated, and unsaturated species, such as alkyl groups, alkenyl groups, aryl groups, aralkyl groups, alkaryl groups, and the like. Unless otherwise indicated, the term "hydrocarbyl" is to be interpreted as including substituted and/or heteroatom-containing hydrocarbyl moieties as well.

By "substituted" as in "substituted alkyl," "substituted aryl," and the like, as alluded to in some of the aforementioned definitions, is typically meant that in the alkyl, aryl, or other moiety, at least one hydrogen atom bound to a carbon (or other) atom is replaced with one or more non-hydrogen substituents. Examples of such substituents include, without limitation: functional groups such as halo, hydroxyl, sulfhydryl, $C_1$–$C_{24}$ alkoxy, $C_5$–$C_{24}$ aryloxy, acyl (including $C_2$–$C_{24}$ alkylcarbonyl (—CO-alkyl) and $C_6$–$C_{24}$ arylcarbonyl (—CO—$C_5$–$C_{24}$ aryl)), haloacyl (including $C_2$–$C_{24}$ haloalkylcarbonyl (—C)—haloalkyl) and $C_6$–$C_{24}$ haloarylcarbonyl (—CO-aryl)), $C_2$–$C_{24}$ thioacyloxy (including —O—(CS)-alkyl and —O—(CS)-aryl), $C_2$–$C_{24}$ thiohaloacyloxy (including —O—(CS)-haloalkyl and —O—(CS)-haloaryl)), acyloxy (—O-acyl), $C_2$–$C_{24}$ alkoxycarbonyl (—(CO)—O-alkyl), $C_6$–$C_{24}$ aryloxycarbonyl (—(CO)—O-aryl), $C_7$–$C_{24}$ alkaryloxycarbonyl (—(CO)—O-alkaryl), $C_7$–$C_{24}$ aralkyloxycarbonyl (—(CO)—O-aralkyl), $C_2$–$C_{24}$ haloalkylcarbonato (—O—(CO)—O-haloalkyl)), $C_6$–$C_{24}$ haloarylcarbonato (—O—(CO)—O-haloaryl), $C_2$–$C_{24}$ alkylthiocarbonato (—O—(CS)—O-alkyl)), $C_6$–$C_{24}$ arylthiocarbonato (—O—(CS)—O-aryl), $C_2$–$C_{24}$ haloalkylthiocarbonato (—O—(CS)—O-haloalkyl), and $C_6$–$C_{24}$ haloarylthiocarbonato (—O—(CS)—O-haloaryl), $C_6$–$C_{24}$ aryloxycarbonyl (—(CO)—O-aryl), halocarbonyl (—CO)—X where X is halo), $C_2$–$C_{24}$ alkylcarbonato (—O—(CO)—O-alkyl), $C_6$–$C_{24}$ arylcarbonato (—O—(CO)—O-aryl), carboxy (—COOH), carboxylato (—COO⁻), carbamoyl (—(CO)—$NH_2$), mono-($C_1$–$C_{24}$ alkyl)-substituted carbamoyl (—(CO)—NH($C_1$–$C_{24}$ alkyl)), di-($C_1$–$C_{24}$ alkyl)-substituted carbamoyl (—(CO)—N($C_1$–$C_{24}$ alkyl)$_2$), mono-($C_6$–$C_{24}$ aryl)-substituted carbamoyl (—(CO)—NH-aryl), di-($C_6$–$C_{24}$ aryl)-substituted carbamoyl (—(CO)—N(aryl)$_2$), di-N—($C_1$–$C_{24}$ alkyl), N—($C_6$–$C_{24}$ aryl)-substituted carbamoyl, thiocarbamoyl (—(CS)—$NH_2$), carbamido (—NH—(CO)—$NH_2$), formyl (—(CO)—H), thioformyl (—(CS)—H), amino (—$NH_2$), mono-($C_1$–$C_{24}$ alkyl)-substituted amino, di-($C_1$–$C_{24}$ alkyl)-substituted amino, mono-($C_5$–$C_{24}$ aryl)-substituted amino, di-($C_5$–$C_{24}$ aryl)-substituted amino, $C_2$–$C_{24}$ alkylamido (—NH—(CO)-alkyl), $C_6$–$C_{24}$ arylamido (—NH—(CO)-aryl), imino (—CR=NH where R=hydrogen, $C_1$–$C_{24}$ alkyl, $C_5$–$C_{24}$ aryl, $C_6$–$C_{24}$ alkaryl, $C_6$–$C_{24}$ aralkyl, etc.), alkylimino (—CR=N(alkyl), where R=hydrogen, $C_1$–$C_{24}$ alkyl, $C_5$–$C_{24}$ aryl, $C_6$–$C_{24}$ alkaryl, $C_6$–$C_{24}$ aralkyl, etc.), arylimino (—CR=N(aryl), where R=hydrogen, $C_1$–$C_{24}$ alkyl, $C_5$–$C_{24}$ aryl, $C_6$–$C_{24}$ alkaryl, $C_6$–$C_{24}$ aralkyl, etc.), nitro (—$NO_2$), nitroso (—NO), sulfo (—$SO_2$—OH), sulfonamido (—$SO_2$—$NH_2$), sulfonato (—$SO_2$—O⁻), $C_1$–$C_{24}$ alkylsulfanyl (—S-alkyl; also termed "alkylthio"), arylsulfanyl (—S-aryl; also termed "arylthio"), $C_1$–$C_{24}$ alkylsulfinyl (—(SO)-alkyl), $C_5$–$C_{24}$ arylsulfinyl (—(SO)-aryl), $C_1$–$C_{24}$ alkylsulfonyl (—$SO_2$-alkyl), $C_5$–$C_{24}$ arylsulfonyl (—$SO_2$-aryl), phosphono (—P(O)(OH)$_2$), phosphonato (—P(O)(O⁻)$_2$), phosphinato (—P(O)(O⁻)), phospho (—$PO_2$), and phosphino (—$PH_2$); and the hydrocarbyl moieties $C_1$–$C_{24}$ alkyl (preferably $C_1$–$C_{18}$ alkyl, more preferably $C_1$–$C_{12}$ alkyl, most preferably $C_1$–$C_6$ alkyl), $C_2$–$C_{24}$ alkenyl (preferably $C_2$–$C_{18}$ alkenyl, more preferably $C_2$–$C_{12}$ alkenyl, most preferably $C_2$–$C_6$ alkenyl), $C_2$–$C_{24}$ alkynyl (preferably $C_2$–$C_{18}$ alkynyl, more preferably $C_2$–$C_{12}$ alkynyl, most preferably $C_2$–$C_6$ alkynyl), $C_5$–$C_{24}$ aryl (preferably $C_5$–$C_{14}$ aryl), $C_6$–$C_{24}$ alkaryl (preferably $C_6$–$C_{18}$ alkaryl), and $C_6$–$C_{24}$ aralkyl (preferably $C_6$–$C_{18}$ aralkyl).

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur, preferably nitrogen or oxygen. Similarly, the term "heteroalkyl" refers to an alkyl substituent that is heteroatom-containing, the term "heterocyclic" refers to a cyclic substituent that is heteroatom-containing, the terms "heteroaryl" and "heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

The terms "halo" and "halogen" are used in the conventional sense to refer to a chloro, bromo, and fluoro or iodo substituent.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When referring to a compound of the invention as a therapeutic or otherwise biologically active agent, applicants intend the term "compound" or "active agent" to encompass not only the specified molecular entity but also its pharmaceutically acceptable, pharmacologically active analogs, including, but not limited to, salts, esters, amides, prodrugs, conjugates, and active metabolites.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. Thus, "treating" a patient with a compound of the invention includes prevention of a particular disorder or adverse physiological event in a susceptible individual as well as treatment of a clinically symptomatic individual by inhibiting or causing regression of a disorder or disease. For example, treatment of cancer encompasses chemoprevention in a patient susceptible to developing cancer (e.g., at a higher risk, as a result of genetic predisposition, environmental factors, or the like) and/or in cancer survivors at risk of cancer recurrence, as well as treatment of a cancer patient dual by inhibiting or causing regression of a disorder or disease.

By the terms "effective amount" and "therapeutically effective amount" of a compound of the invention is meant a nontoxic but sufficient amount of the drug or agent to provide the desired effect.

The term "dosage form" denotes any form of a pharmaceutical composition that contains an amount of active agent sufficient to achieve a therapeutic effect with a single administration. When the formulation is a tablet or capsule, the dosage form is usually one such tablet or capsule. The frequency of administration that will provide the most effective results in an efficient manner without overdosing will vary with the characteristics of the particular active agent, including both its pharmacological characteristics and its physical characteristics, such as hydrophilicity.

The term "controlled release" refers to a drug-containing formulation or fraction thereof in which release of the drug is not immediate, i.e., with a "controlled release" formulation, administration does not result in immediate release of the drug into an absorption pool. The term is used interchangeably with "nonimmediate release" as defined in *Remington: The Science and Practice of Pharmacy, Nineteenth Ed.* (Easton, Pa.: Mack Publishing Company, 1995). In general, the term "controlled release" as used herein includes sustained release and delayed release formulations.

The term "sustained release" (synonymous with "extended release") is used in its conventional sense to refer to a drug formulation that provides for gradual release of a drug over an extended period of time, and that preferably, although not necessarily, results in substantially constant blood levels of a drug over an extended time period.

The term "pharmaceutically acceptable" means that a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration. "Pharmacologically active" (or simply "active") as in a "pharmacologically active" derivative or analog, refers to a derivative or analog having the same type of pharmacological activity as the parent compound and approximately equivalent in degree.

II. Compounds of the Invention

The present invention provides new compounds useful as therapeutic agents for the treatment of cancer or other disorders responsive to selective apoptosis. One of the novel compounds provided by the present invention is a purified, isolated form of isoapoptolidin, which is a ring-expanded macrolide isomer of apoptolidin having the structure of formula (I)

Although apoptolidin can be purified chromatographically, isoapoptolidin does not elute without some apoptolidin contamination. Example 1 describes an enrichment procedure required to purify isolated isoapoptolidin and the techniques that permit analysis of the resulting purified crystals.

Other compounds of the present invention include functionalized derivatives of isoapoptolidin, apoptolidin, and deglycosylated isoapoptolidin, as well as stereoisomers thereof and deglycosylated isoapoptolidin per se.

Functionalized isoapoptolidin compounds of the invention are compounds that correspond to isoapoptolidin or a stereoisomer thereof in which at least one hydroxyl group within the molecule is replaced with a substituent selected from:

(a) $C_1$–$C_{24}$ hydrocarbyloxy, optionally substituted with one or more halogen atoms, e.g., $C_1$–$C_{24}$ alkoxy (—O—($C_1$–$C_{24}$ alkyl)), $C_6$–$C_{24}$ aralkoxy (—O—($C_6$–$C_{24}$ aralkyl)), $C_6$–$C_{24}$ alkaryloxy (—O—($C_6$–$C_{24}$ alkaryl)), $C_1$–$C_{24}$ haloalkoxy (—O—($C_1$–$C_{24}$ haloalkyl)), and $C_6$–$C_{24}$ haloaralkoxy (—O—($C_6$–$C_{24}$ haloalkoxy), preferably $C_1$–$C_{12}$ hydrocarbyloxy, optionally substituted with one or more halogen atoms, e.g., $C_1$–$C_{12}$ alkoxy (—O—($C_1$–$C_{12}$ alkyl)), $C_6$–$C_{12}$ aralkoxy (—O—($C_6$–$C_{12}$ aralkyl)), $C_6$–$C_{12}$ alkaryloxy (—O—($C_6$–$C_{12}$ alkaryl)), $C_1$–$C_{12}$ haloalkoxy (—O—($C_1$–$C_{12}$ haloalkyl)), and $C_6$–$C_{12}$ haloaralkoxy (—O—($C_6$–$C_{12}$ haloalkaryl));

(b) $C_2$–$C_{25}$ acyloxy (—O—(CO)—($C_1$–$C_{24}$ hydrocarbyl)), e.g., —O—(CO)—($C_1$–$C_{24}$ alkyl), —O—(CO)—($C_5$–$C_{24}$ aryl), —O—(CO)—($C_6$–$C_{24}$ aralkyl), and —O—(CO)—($C_6$–$C_{24}$ alkaryl)), preferably $C_2$–$C_{13}$ acyloxy (—O—(CO)—($C_1$–$C_{12}$ hydrocarbyl)), e.g., —O—(CO)—($C_1$$C_{12}$ alkyl), —O—(CO)—($C_5$–$C_{12}$ aryl), —O—(CO)—($C_6$–$C_{12}$ aralkyl), and —O—(CO)—($C_6$–$C_{12}$ alkaryl));

(c) $C_2$–$C_{25}$ haloacyloxy (—O—(CO)—($C_2$–$C_{24}$ halohydrocarbyl)), e.g., —O—(CO)—($C_1$–$C_{24}$ haloalkyl), —O—(CO)—($C_5$–$C_{24}$ haloaryl), —O—(CO)—($C_5$–$C_{24}$ haloaralkyl), and —O—(CO)—($C_5$–$C_{24}$ haloalkaryl), preferably $C_2$–$C_{13}$ haloacyloxy (—O—(CO)—($C_2$–$C_{12}$ halohydrocarbyl)), e.g., —O—(CO)—($C_1$–$C_{12}$ haloalkyl), —O—(CO)—($C_5$–$C_{12}$ haloaryl), —O—(CO)—($C_5$–$C_{12}$ haloaralkyl), and —O—(CO)—($C_5$–$C_{12}$ haloalkaryl);

(I)

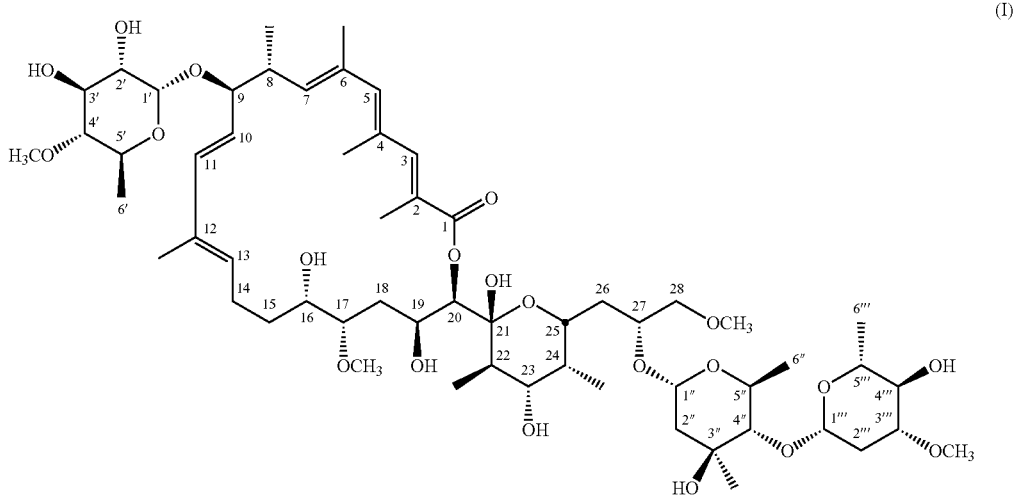

(d) $C_2$–$C_{25}$ thioacyloxy (—O—(CS)—($C_2$–$C_{24}$ hydrocarbyl)), e.g., —O—(CS)—($C_1$–$C_{24}$ alkyl), —O—(CS)—($C_5$–$C_{24}$ aryl), —O—(CS)—($C_5$–$C_{24}$ aralkyl), and —O—(CS)—($C_5$–$C_{24}$ alkaryl), preferably $C_2$–$C_{13}$ thioacyloxy (—O—(CS)—($C_2$–$C_{12}$ hydrocarbyl)), e.g., —O—(CS)—($C_1$–$C_{12}$ alkyl), —O—(CS)—($C_5$–$C_{12}$ aryl), —O—(CS)—($C_5$–$C_{12}$ aralkyl), and —O—(CS)—($C_5$–$C_{12}$ alkaryl);

(e) $C_2$–$C_{25}$ thiohaloacyloxy (—O—(CS)—($C_2$–$C_{24}$ hydrocarbyl)), e.g., —O—(CS)—($C_1$–$C_{24}$ haloalkyl), —O—(CS)—($C_5$–$C_{24}$ haloaryl), —O—(CS)—($C_5$–$C_{24}$ haloaralkyl), and —O—(CS)—($C_5$–$C_{24}$ haloalkaryl), preferably $C_2$–$C_{13}$ thiohaloacyloxy (—O—(CS)—($C_2$–$C_{12}$ hydrocarbyl)), e.g., —O—(CS)—($C_1$–$C_{12}$ haloalkyl), —O—(CS)—($C_5$–$C_{12}$ haloaryl), —O—(CS)—($C_5$–$C_{12}$ haloaralkyl), and —O—(CS)—($C_5$–$C_{12}$ haloalkaryl);

(f) $C_2$–$C_{25}$ carbonato (—O—(CO)—O—($C_1$–$C_{24}$ hydrocarbyl)), e.g., $C_2$–$C_{25}$ alkylcarbonato (—O—(CO)—O—($C_1$–$C_{24}$ alkyl)), $C_6$–$C_{25}$ arylcarbonato (—O—(CO)—O—($C_5$–$C_{24}$ aryl)), $C_6$–$C_{25}$ aralkylcarbonato (—O—(CO)—O—($C_5$–$C_{24}$ aralkyl)), and $C_6$–$C_{25}$ alkarylcarbonato (—O—(CO)—O—($C_5$–$C_{24}$ alkaryl)), preferably $C_2$–$C_{13}$ carbonato (—O—(CO)—O—($C_1$–$C_{12}$ hydrocarbyl)), e.g., $C_2$–$C_{13}$ alkylcarbonato (—O—(CO)—O—($C_1$–$C_{12}$ alkyl)), $C_6$–$C_{13}$ arylcarbonato (—O—(CO)—O—($C_5$–$C_{12}$ aryl)), $C_6$–$C_{13}$ aralkylcarbonato (—O—(CO)—O—($C_5$–$C_{12}$ aralkyl)), and $C_6$–$C_{13}$ alkarylcarbonato (—O—(CO)—O—($C_5$–$C_{12}$ alkaryl));

(g) halogenated $C_2$–$C_{25}$ carbonato (—O—(CO)—O—($C_1$–$C_{24}$ halohydrocarbyl)), e.g., $C_2$–$C_{25}$ haloalkylcarbonato (—O—(CO)—O—($C_1$–$C_{24}$ haloalkyl)), $C_6$–$C_{25}$ haloarylcarbonato (—O—(CO)—O—($C_5$–$C_{24}$ haloaryl)), $C_6$–$C_{25}$ haloaralkylcarbonato (—O—(CO)—O—($C_5$–$C_{24}$ haloaralkyl)), and $C_6$–$C_{25}$ haloalkarylcarbonato (—O—(CO)—O—($C_5$–$C_{24}$ haloalkaryl)), preferably halogenated $C_2$–$C_{13}$ carbonato (—O—(CO)—O—($C_1$–$C_{12}$ halohydrocarbyl)), e.g., $C_2$–$C_{13}$ haloalkylcarbonato (—O—(CO)—O—($C_1$–$C_{12}$ haloalkyl)), $C_6$–$C_{13}$ haloarylcarbonato (—O—(CO)—O—($C_5$–$C_{12}$ haloaryl)), $C_6$–$C_{13}$ haloaralkylcarbonato (—O—(CO)—O—($C_5$–$C_{12}$ haloaralkyl)), and $C_6$–$C_{13}$ haloalkarylcarbonato (—O—(CO)—O—($C_5$–$C_{12}$ haloalkaryl));

(h) $C_2$–$C_{25}$ thiocarbonato (—O—(CS)—O—($C_1$–$C_{24}$ hydrocarbyl)), e.g., $C_2$–$C_{25}$ alkylcarbonato (—O—(CS)—O—($C_1$–$C_{24}$ alkyl)), $C_6$–$C_{25}$ arylcarbonato (—O—(CS)—O—($C_5$–$C_{24}$ aryl)), $C_6$–$C_{25}$ aralkylcarbonato (—O—(CS)—O—($C_5$–$C_{24}$ aralkyl)), and $C_6$–$C_{25}$ alkarylcarbonato (—O—(CS)—O—($C_5C_{24}$ alkaryl)), preferably $C_2$–$C_{13}$ thiocarbonato (—O—(CS)—O—($C_1$–$C_{12}$ hydrocarbyl)), e.g., $C_2$–$C_{13}$ alkylcarbonato (—O—(CS)—O—($C_1$–$C_{12}$ alkyl)), $C_6$–$C_{13}$ arylcarbonato (—O—(CS)—O—($C_5$–$C_{12}$ aryl)), $C_6$–$C_{13}$ aralkylcarbonato (—O—(CS)—O—($C_5$–$C_{12}$ aralkyl)), and $C_6$–$C_{13}$ alkarylcarbonato (—O—(CS)—O—($C_5$–$C_{12}$ alkaryl));

(i) halogenated $C_2$–$C_{25}$ thiocarbonato (—O—(CS)—O—($C_1$–$C_{24}$ halohydrocarbyl)), e.g., $C_2C_{25}$ haloalkylthiobonato (—O—(CS)—O—($C_1$–$C_{24}$ haloalkyl)), $C_6$–$C_{25}$ haloarylthiocarbonato (—O—(CS)—O—($C_5$–$C_{24}$ haloaryl)), $C_6$–$C_{25}$ haloaralkylthiocarbonato (—O—(CS)—O—($C_5$–$C_{24}$ haloaralkyl)), and $C_6$–$C_{25}$ haloalkarylthiocarbonato (—O—(CS)—O—($C_5$–$C_{24}$ haloalkaryl)), preferably halogenated $C_2$–$C_{13}$ thiocarbonato (—O—(CS)—O—($C_1$–$C_{12}$ halohydrocarbyl)), e.g., $C_2$–$C_{13}$ haloalkylthiocarbonato (—O—(CS)—O—($C_1$–$C_{12}$ haloalkyl)), $C_6$–$C_{13}$ haloarylthiocarbonato (—O—(CS)—O—($C_5$–$C_{12}$ haloaryl)), $C_6$–$C_{13}$ haloaralkylthiocarbonato (—O—(CS)—O—($C_5$–$C_{12}$ haloaralkyl)), and $C_6$–$C_{13}$ haloalkarylthiocarbonato (—O—(CS)—O—($C_5$–$C_{12}$ haloalkaryl));

(j) carbamoyloxy (—O—(CO)—$NH_2$), mono-($C_1$–$C_{24}$ alkyl)-substituted carbamoyloxy (—O—(CO)—NH($C_1$–$C_{24}$ alkyl)), di-($C_1$–$C_{24}$ alkyl)-substituted carbamoyloxy (—O—(CO)—N($C_1$–$C_{24}$ alkyl)$_2$), mono-($C_6$–$C_{24}$ aryl)-substituted carbamoyloxy (—O—(CO)—NH-aryl), di-($C_6$–$C_{24}$ aryl)-substituted carbamoyloxy (—O—(CO)—N(aryl)$_2$), and di-N—($C_1$–$C_{24}$ alkyl), N—($C_6$–$C_{24}$ aryl)-substituted carbamoyloxy, preferably carbamoyloxy (—O—(CO)—$NH_2$), mono-($C_1$–$C_{12}$ alkyl)-substituted carbamoyloxy (—O—(CO)—NH($C_1$–$C_{12}$ alkyl)), di-($C_1$–$C_{12}$ alkyl)-substituted carbamoyloxy (—O—(CO)—N($C_1$–$C_{12}$ alkyl)$_2$), mono-($C_6$–$C_{12}$ aryl)-substituted carbamoyloxy (—O—(CO)—NH-aryl), di-($C_6$–$C_{12}$ aryl)-substituted carbamoyloxy (—O—(CO)—N(aryl)$_2$), and di-N—($C_1$–$C_{12}$ alkyl), N—($C_6$–$C_{12}$ aryl)-substituted carbamoyloxy (k) thiocarbamoyloxy (—O—(CS)—$NH_2$), mono-($C_1$–$C_{24}$ alkyl)-substituted thiocarbamoyloxy (—O—(CS)—NH($C_1$–$C_{24}$ alkyl)), di-($C_1$–$C_{24}$ alkyl)-substituted thiocarbamoyloxy (—O—(CS)—N($C_1$–$C_{24}$ alkyl)$_2$), mono-($C_6$–$C_{24}$ aryl)-substituted thiocarbamoyloxy (—O—(CS)—NH-aryl), di-($C_6$–$C_{24}$ aryl)-substituted carbamoyloxy (—O—(CS)—N(aryl)$_2$), and di-N—($C_1$–$C_{24}$ alkyl), N—($C_6$–$C_{24}$ aryl)-substituted thiocarbamoyloxy, preferably thiocarbamoyloxy (—O—(CS)—$NH_2$), mono-($C_1$–$C_{12}$ alkyl)-substituted thiocarbamoyloxy (—O—(CS)—NH($C_1$–$C_{12}$ alkyl)), di-($C_1$–$C_{12}$ alkyl)-substituted thiocarbamoyloxy (—O—(CS)—N($C_1$–$C_{12}$ alkyl)$_2$), mono-($C_6$–$C_{12}$ aryl)-substituted thiocarbamoyloxy (—O—(CS)—NH-aryl), di-($C_6$–$C_{12}$ aryl)-substituted thiocarbamoyloxy (—O—(CS)—N(aryl)$_2$), and di-N—($C_1$–$C_{12}$ alkyl), N—($C_6$–$C_{12}$ aryl)-substituted thiocarbamoyloxy;

(l) sulfamoyloxy (—O—$SO_2$—$NH_2$), mono-($C_1$–$C_{24}$ alkyl)-substituted sulfamoyloxy (—O—$SO_2$—NH($C_1$–$C_{24}$ alkyl)), di-($C_1$–$C_{24}$ alkyl)-substituted sulfamoyloxy (—O—$SO_2$—N($C_1$–$C_{24}$ alkyl)$_2$), mono-($C_6$–$C_{24}$ aryl)-substituted sulfamoyloxy (—O—$SO_2$—NH-aryl), di-($C_6$–$C_{24}$ aryl)-substituted sulfamoyloxy (—O—$SO_2$—N(aryl)$_2$), and di-N—($C_1$–$C_{24}$ alkyl), N—($C_6$–$C_{24}$ aryl)-substituted sulfamoyloxy, preferably sulfamoyloxy (—O—$SO_2$—$NH_2$), mono-($C_1$–$C_{12}$ alkyl)-substituted sulfamoyloxy (—O—$SO_2$—NH($C_1$–$C_{12}$ alkyl)), di-($C_1$–$C_{12}$ alkyl)-substituted sulfamoyloxy (—O—$SO_2$—N($C_1$–$C_{12}$ alkyl)$_2$), mono-($C_6$–$C_{12}$ aryl)-substituted sulfamoyloxy (—O—$SO_2$—NH-aryl), di-($C_6$–$C_{12}$ aryl)-substituted sulfamoyloxy (—O—$SO_2$—N(aryl)$_2$), and di-N—($C_1$–$C_{12}$ alkyl), N—($C_6$–$C_{12}$ aryl)-substituted sulfamoyloxy and (m) protected hydroxyl groups such as tri-($C_1$–$C_{12}$ hydrocarbyl)-substituted silyloxy, preferably tri-($C_1$–$C_4$ alkyl)silyloxy, and substituted methyl ethers such as ($C_1$–$C_6$ alkoxy)methyl ethers (e.g., methoxymethyl ether (—O—$CH_2$—O—$CH_3$) and t-butoxymethyl ether (—O—$CH_2$—O—C($CH_3$)$_3$)) and ($C_1$–$C_6$ alkylthio)methyl ethers such as methylthiomethyl ether (—O—$CH_2$—S—$CH_3$), wherein any of (a) through (m) may be substituted and/or heteroatom-containing where the functional group permits.

Preferred functionalized isoapoptolidin compounds of the invention are those wherein at least one hydroxyl group of isoapoptolidin per se is replaced with $C_1$–$C_{12}$ hydrocarbyl, $C_1$–$C_{13}$ acyl, or a protected hydroxyl group. Of these, the more preferred functionalized isoapoptolidin compounds are exemplified by the structure of formula (II)

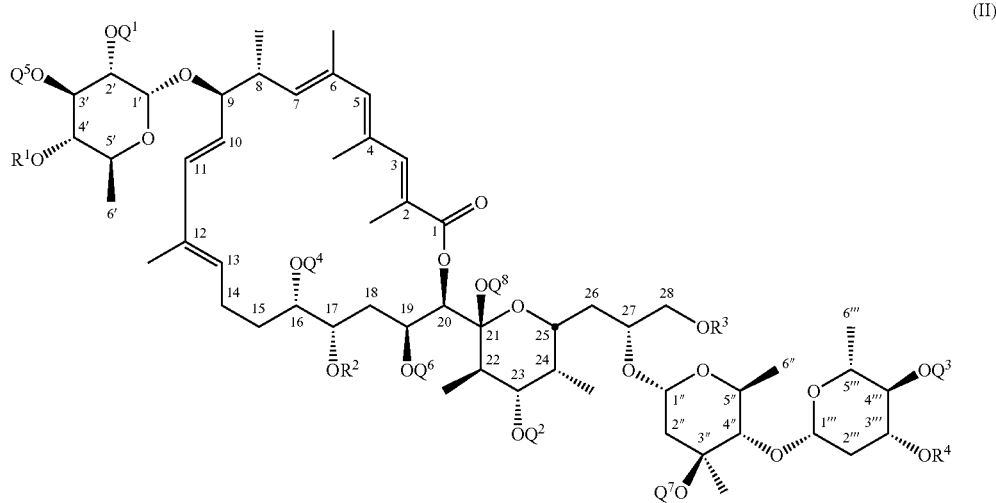

(II)

or are stereoisomers thereof, wherein $Q^1$, $Q^2$, $Q^3$, $Q^4$, $Q^5$, $Q^6$, $Q^7$, and $Q^8$ are selected from H, $C_1$–$C_{12}$ hydrocarbyl (including substituted and/or heteroatom-containing $C_1$–$C_{12}$ hydrocarbyl), acyl of the formula —(CO)—$R^5$ wherein $R^5$ is $C_1$–$C_{12}$ hydrocarbyl (including substituted and/or heteroatom-containing $C_1$–$C_{12}$ hydrocarbyl), and hydroxyl-protecting groups. In formula (II), $R^1$, $R^2$, $R^3$, and $R^4$, which are methyl groups in isoapoptolidin, are independently selected from $C_1$–$C_{12}$ alkyl (including substituted and/or heteroatom-containing $C_1$–$C_{12}$ alkyl) and H.

More preferred functionalized isoapoptolidin derivatives of the invention are those of formula (II) wherein $Q^1$, $Q^2$, $Q^3$, $Q^4$, $Q^5$, $Q^6$, $Q^7$, and $Q^8$ are selected from H, $C_1$–$C_6$ hydrocarbyl (including substituted and/or heteroatom-containing $C_1$–$C_6$ hydrocarbyl), —(CO)—$R^5$ wherein $R^5$ is $C_1$–$C_6$ hydrocarbyl (including substituted and/or heteroatom-containing $C_1$–$C_6$ hydrocarbyl), and —Si($R^6R^7R^8$) wherein $R^6$, $R^7$, and $R^8$ are $C_1$–$C_6$ hydrocarbyl, and $R^1$, $R^2$, $R^3$, and $R^4$ are $C_1$–$C_4$ alkyl (including substituted and/or heteroatom-containing $C_1$–$C_4$ alkyl).

Still more preferred functionalized isoapoptolidin derivatives of the invention are those of the formula (II) wherein $Q^1$, $Q^2$, $Q^3$, $Q^4$, $Q^5$, $Q^6$, $Q^7$, and $Q^8$ are independently selected from H, $C_1$–$C_6$ alkyl (including substituted and/or heteroatom-containing alkyl), —(CO)—$R^5$ wherein $R^5$ is $C_1$–$C_4$ or benzyl, and —Si($R^6R^7R^8$) wherein $R^6$, $R^7$, and $R^8$ are all methyl or are all ethyl, and $R^1$, $R^2$, $R^3$, and $R^4$ are methyl.

Representative functionalized isoapoptolidin derivatives of the invention which are particularly preferred herein are compounds of formula (II) wherein:

$Q^1$ is —(CO)—$R^5$ and $Q^2$, $Q^3$, $Q^4$, $Q^5$, $Q^6$, $Q^7$, and $Q^8$ are H;

$Q^2$ and $Q^3$ are —(CO)—$R^5$ and $Q^1$, $Q^4$, $Q^5$, $Q^6$, $Q^7$, and $Q^8$ are H;

$Q^3$ is —(CO)—$R^5$ and $Q^1$, $Q^2$, $Q^4$, $Q^5$, $Q^6$, $Q^7$, and $Q^8$ are H;

$Q^4$ is —(CO)—$R^5$ and $Q^1$, $Q^2$, $Q^3$, $Q^5$, $Q^6$, $Q^7$, and $Q^8$ are H;

$Q^5$ is —(CO)—$R^5$ and $Q^1$, $Q^2$, $Q^3$, $Q^4$, $Q^6$, $Q^7$ and $Q^8$ are H;

$Q^6$ is —(CO)—$R^5$ and $Q^1$, $Q^2$, $Q^3$, $Q^4$, $Q^5$, $Q^7$ and $Q^8$ are H;

$Q^6$ is $C_1$–$C_6$ alkyl and $Q^1$, $Q^2$, $Q^3$, $Q^4$, $Q^5$, $Q^7$ and $Q^8$ are H; or $Q^8$ is $C_1$–$C_6$ alkyl and $Q^1$, $Q^2$, $Q^3$, $Q^4$, $Q^5$, $Q^6$ and $Q^7$ are H, and the most preferred functionalized isoapoptolidin derivatives of the invention are compounds of formula (II) wherein:

$Q^1$ is benzoyl and $Q^2$, $Q^3$, $Q^4$, $Q^5$, $Q^6$, $Q^7$, and $Q^8$ are H;

$Q^2$ and $Q^3$ are acetyl and $Q^1$, $Q^4$, $Q^5$, $Q^6$, $Q^7$, and $Q^8$ are H;

$Q^3$ is acetyl and $Q^1$, $Q^2$, $Q^4$, $Q^5$, $Q^6$, $Q^7$ and $Q^8$ are H;

$Q^4$ is acetyl and $Q^1$, $Q^2$, $Q^3$, $Q^5$, $Q^6$, $Q^7$ and $Q^8$ are H;

$Q^5$ is acetyl and $Q^1$, $Q^2$, $Q^3$, $Q^4$, $Q^6$, $Q^7$, and $Q^8$ are H;

$Q^6$ is acetyl and $Q^1$, $Q^2$, $Q^3$, $Q^4$, $Q^5$, $Q^7$, and $Q^8$ are H;

$Q^6$ is methyl and $Q^1$, $Q^2$, $Q^3$, $Q^4$, $Q^5$, $Q^7$, and $Q^8$ are H; or $Q^8$ is methyl and $Q^1$, $Q^2$, $Q^3$, $Q^4$, $Q^5$, $Q^6$, and $Q^7$ are H.

The functionalized apoptolidin compounds of the invention correspond to apoptolidin per se or a stereoisomer thereof, in which at least one hydroxyl group within the molecule is replaced with a substituent selected from (a) through (j) above. Preferred functionalized apoptolidin compounds of the invention have the structure of formula (III)

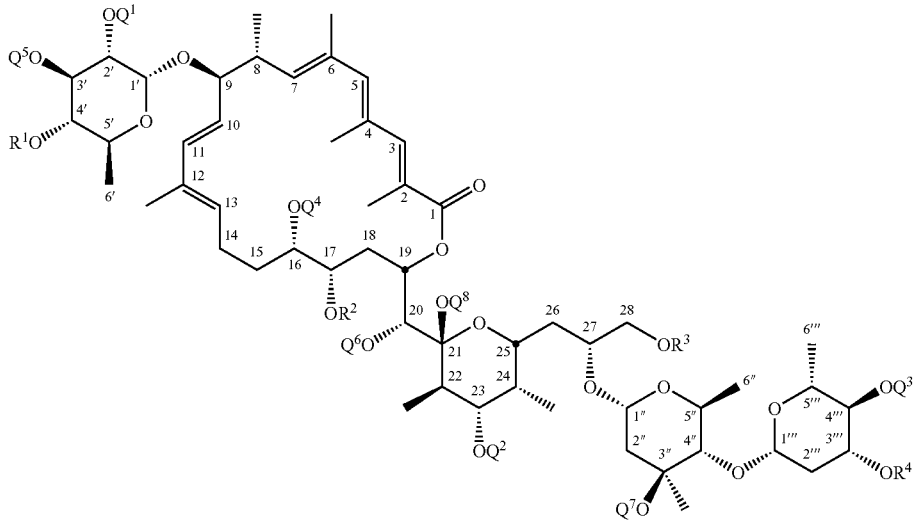

(III)

wherein $Q^1$, $Q^2$, $Q^3$, $Q^4$, $Q^5$, $Q^6$, $Q^7$, $Q^8$, $R^1$, $R^2$, $R^3$, and $R^4$ are defined as for the functionalized isoapoptolidin compounds of formula (II), with the proviso that at least one of $Q^1$, $Q^2$, $Q^3$, $Q^4$, $Q^5$, $Q^6$, $Q^7$, and $Q^8$ is other than H when $R^1$, $R^2$, $R^3$, and $R^4$ are methyl and the functionalized apoptolidin compound has the stereoisomeric configuration shown in formula (III).

More preferred functionalized apoptolidin derivatives of the invention, as with the functionalized isoapoptolidin compound of formula (II), are, accordingly, those of formula (III) wherein $Q^1$, $Q^2$, $Q^3$, $Q^4$, $Q^5$, $Q^6$, $Q^7$, and $Q^8$ are selected from H, $C_1$–$C_6$ hydrocarbyl, —(CO)—$R^5$ wherein $R^5$ is $C_1$–$C_6$ hydrocarbyl, and —Si($R^6R^7R^8$) wherein $R^6$, $R^7$, and $R^8$ are $C_1$–$C_6$ hydrocarbyl, with the proviso that at least one of $Q^1$, $Q^2$, $Q^3$, $Q^4$, $Q^5$, $Q^6$, $Q^7$, and $Q^8$ is other than H, and $R^1$, $R^2$, $R^3$, and $R^4$ are $C_1$–$C_4$ alkyl.

Still more preferred functionalized apoptolidin derivatives of the invention are those of the formula (III) wherein $Q^1$, $Q^2$, $Q^3$, $Q^4$, $Q^5$, $Q^6$, $Q^7$, and $Q^8$ are selected from H, $C_1$–$C_6$ alkyl, —(CO)—$R^5$ wherein $R^5$ is lower alkyl or benzyl, and —Si($R^6R^7R^8$) wherein $R^6$, $R^7$, and $R^8$ are all methyl or are all ethyl, with the proviso that at least one of $Q^1$, $Q^2$, $Q^3$, $Q^4$, $Q^5$, $Q^6$, $Q^7$, and $Q^8$ is other than H, and $R^1$, $R^2$, $R^3$, and $R^4$ are methyl.

Representative functionalized apoptolidin derivatives of the invention which are particularly preferred herein are compounds of formula (III) wherein:

$Q^1$ is —(CO)—$R^5$ and $Q^2$, $Q^3$, $Q^4$, $Q^5$, $Q^6$, $Q^7$, and $Q^8$ are H;

$Q^2$ and $Q^3$ are —(CO)—$R^5$ and $Q^1$, $Q^4$, $Q^5$, $Q^6$, $Q^7$, and $Q^8$ are H;

$Q^3$ is —(CO)—$R^5$ and $Q^1$, $Q^2$, $Q^4$, $Q^5$, $Q^6$, $Q^7$, and $Q^8$ are H;

$Q^4$ is —(CO)—$R^5$ and $Q^1$, $Q^2$, $Q^3$, $Q^5$, $Q^6$, $Q^7$, and $Q^8$ are H;

$Q^5$ is —(CO)—$R^5$ and $Q^1$, $Q^2$, $Q^3$, $Q^4$, $Q^6$, $Q^7$, and $Q^8$ are H;

$Q^6$ is —(CO)—$R^5$ and $Q^1$, $Q^2$, $Q^3$, $Q^4$, $Q^5$, $Q^7$, and $Q^8$ are H;

$Q^6$ is $C_1$–$C_6$ alkyl and $Q^1$, $Q^2$, $Q^3$, $Q^4$, $Q^5$, $Q^7$, and $Q^8$ are H; or $Q^8$ is $C_1$–$C_6$ alkyl and $Q^1$, $Q^2$, $Q^3$, $Q^4$, $Q^5$, $Q^6$, and $Q^7$ are H, and the most preferred functionalized apoptolidin derivatives of the invention are compounds of formula (III) wherein:

$Q^1$ is benzoyl and $Q^2$, $Q^3$, $Q^4$, $Q^5$, $Q^6$, $Q^7$, and $Q^8$ are H;

$Q^2$ and $Q^3$ are acetyl and $Q^1$, $Q^4$, $Q^5$, $Q^6$, $Q^7$, and $Q^8$ are H;

$Q^3$ is acetyl and $Q^1$, $Q^2$, $Q^4$, $Q^5$, $Q^6$, $Q^7$, and $Q^8$ are H;

$Q^4$ is acetyl and $Q^1$, $Q^2$, $Q^3$, $Q^5$, $Q^6$, $Q^7$, and $Q^8$ are H;

$Q^5$ is acetyl and $Q^1$, $Q^2$, $Q^3$, $Q^4$, $Q^6$, $Q^7$, and $Q^8$ are H;

$Q^6$ is acetyl and $Q^1$, $Q^2$, $Q^3$, $Q^4$, $Q^5$, $Q^7$, and $Q^8$ are H;

$Q^6$ is methyl and $Q^1$, $Q^2$, $Q^3$, $Q^4$, $Q^5$, $Q^7$ and $Q^8$ are H; or $Q^8$ is methyl and $Q^1$, $Q^2$, $Q^3$, $Q^4$, $Q^5$, $Q^6$ and $Q^7$ are H.

The deglycosylated isoapoptolidin compounds of the invention include deglycosylated isoapoptolidin per se as well as functionalized analogs thereof, wherein "deglycosylated" refers to a truncated structure in which the oleandrose and olivomycose sugars are absent. Deglycosylated apoptolidin is described in U.S. Patent Application Publication No. 2002/0049168 to Khosla et al. and U.S. Patent Application Publication No. 2002/0077300 to Khosla et al., now U.S. Pat. No. 6,548,485. The deglycosylated isoapoptolidin compounds of the invention have the structure of formula (IV)

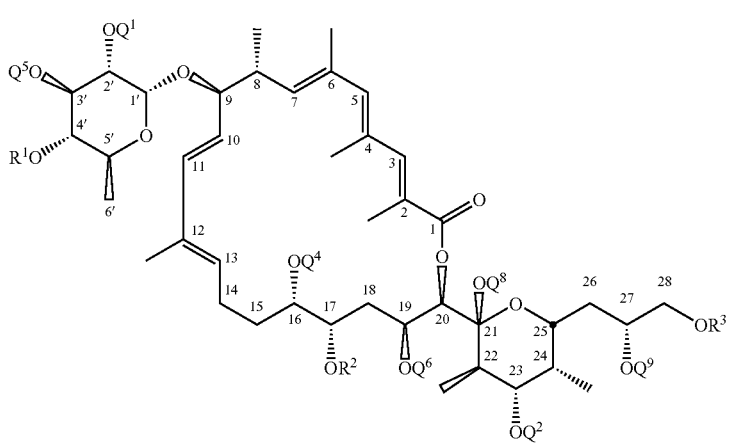

(IV)

wherein $Q^1$, $Q^2$, $Q^4$, $Q^5$, $Q^6$, $Q^8$, and $Q^9$ are independently selected from H, $C_1$–$C_{12}$ hydrocarbyl, —(CO)—$R^5$ wherein $R^5$ is $C_1$–$C_{12}$ hydrocarbyl, and hydroxyl-protecting groups, and $R^1$, $R^2$, and $R^3$ are independently selected from $C_1$–$C_{12}$ alkyl and H.

More preferred deglycosylated isoapoptolidin compounds of the invention are those of formula (IV) wherein $Q^1$, $Q^2$, $Q^4$, $Q^5$, $Q^6$, $Q^8$, and $Q^9$ are selected from H, $C_1$–$C_6$ hydrocarbyl, —(CO)—$R^5$ wherein $R^5$ is $C_1$–$C_6$ hydrocarbyl, and —Si($R^6R^7R^8$) wherein $R^6$, $R^7$, and $R^8$ are $C_1$–$C_6$ hydrocarbyl, and $R^1$, $R^2$, $R^3$, and $R^4$ are $C_1$–$C_4$ alkyl.

Still more preferred deglycosylated isoapoptolidin compounds of the invention are those of formula (IV) wherein $Q^1$, $Q^2$, $Q^4$, $Q^5$, $Q^6$, $Q^8$, and $Q^9$ are selected from H, $C_1$–$C_6$ alkyl, —(CO)—$R^5$ wherein $R^5$ is lower alkyl or benzyl, and —Si($R^6R^7R^8$) wherein $R^6$, $R^7$, and $R^8$ are all methyl or are all ethyl.

Representative deglycosylated isoapoptolidin compounds of the invention which are particularly preferred herein are compounds of formula (IV) wherein:

$Q^1$ is —(CO)—$R^5$ and $Q^2$, $Q^4$, $Q^5$, $Q^6$, $Q^8$, and $Q^9$ are H;
$Q^2$ is —(CO)—$R^5$ and $Q^1$, $Q^4$, $Q^5$, $Q^6$, $Q^8$, and $Q^9$ are H;
$Q^4$ is —(CO)—$R^5$ and $Q^1$, $Q^2$, $Q^5$, $Q^6$, $Q^8$ and $Q^9$ are H;
$Q^5$ is —(CO)—$R^5$ and $Q^1$, $Q^2$, $Q^4$, $Q^6$, $Q^8$ and $Q^9$ are H;
$Q^6$ is —(CO)—$R^5$ and $Q^1$, $Q^2$, $Q^4$, $Q^5$, $Q^8$, and $Q^9$ are H;
$Q^6$ is $C_1$–$C_6$ alkyl and $Q^1$, $Q^2$, $Q^4$, $Q^5$, $Q^8$, and $Q^9$ are H; or
$Q^8$ is $C_1$–$C_6$ alkyl and $Q^1$, $Q^2$, $Q^4$, $Q^5$, $Q^6$, and $Q^9$ are H, and the most preferred deglycosylated isoapoptolidin compounds of the invention are compounds of formula (IV) wherein:

$Q^1$ is benzoyl and $Q^2$, $Q^4$, $Q^5$, $Q^6$, $Q^8$, and $Q^9$ are H;
$Q^2$ and are acetyl and $Q^1$, $Q^4$, $Q^5$, $Q^6$, $Q^8$, and $Q^9$ are H;
$Q^4$ is acetyl and $Q^1$, $Q^2$, $Q^5$, $Q^6$, $Q^8$ and $Q^9$ are H;
$Q^5$ is acetyl and $Q^1$, $Q^2$, $Q^4$, $Q^6$, $Q^8$ and $Q^9$ are H;
$Q^6$ is acetyl and $Q^1$, $Q^2$, $Q^3$, $Q^4$, and $Q^6$ are H;
$Q^6$ is methyl and $Q^1$, $Q^2$, $Q^3$, $Q^4$, and $Q^5$ are H;
$Q^8$ is methyl and $Q^1$, $Q^2$, $Q^4$, $Q^5$, $Q^6$, and $Q^9$ are H.

In addition to the foregoing, it is also to be understood that within the context of the present invention, adjacent (1,2-) diols in any one of the compounds of formulae (II), (III), and (IV) may be linked to form cyclic ethers. For example, cyclic ethers may be prepared by linking together $Q^1$ and $Q^5$. As will be appreciated by those of ordinary skill in the art, the reaction is readily carried out by treating the diol form of the compound with triphosgene or acetone to yield a cyclic carbonate or acetonide group, respectively.

The compounds of the invention also include derivatives in which at least one of the carbon-carbon double bonds of the compounds of formulae (II), (III), and (IV) is be rendered saturated through, for example, catalytic hydrogenation or nucleophilic addition. In another embodiment, the C-10/C-13 diene of the compounds of formulae (II), (III), and (IV) is reacted with a dienophile to yield Diels-Alder adducts. In one example, the reaction of the C-10/C-13 diene of apoptolidin with an N-halosuccinimide results in a compound having the structure of formula (V)

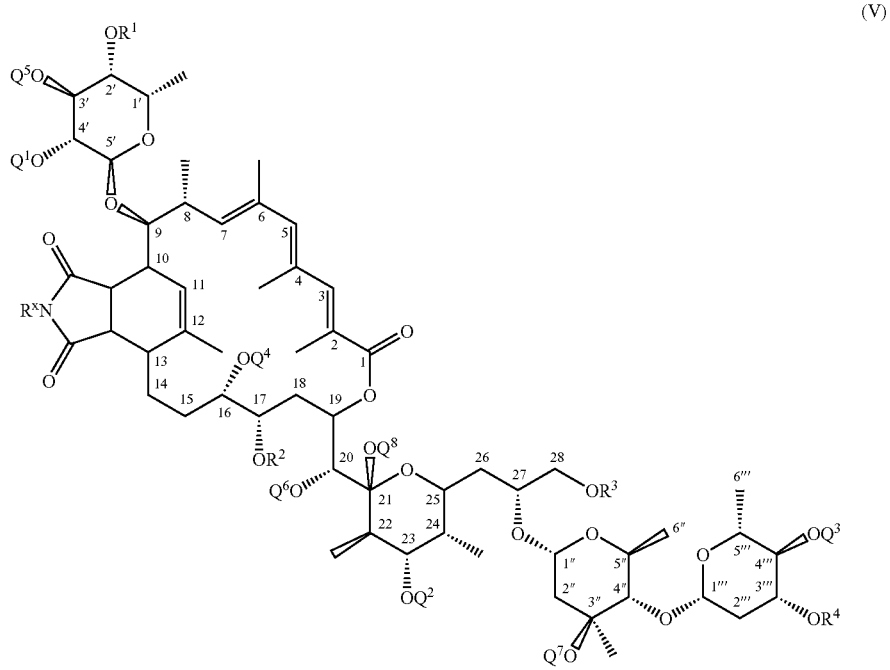

(V)

wherein $R^x$ is a halogen atom. The dienophile may be, for example, N-bromosuccinimide (NBS), N-iodosuccinimide (NIS), or N-chlorosuccinimide (NCS).

Additional compounds within the scope of the invention result from the cleavage or decomposition of apoptolidin. Such structures serve to facilitate a divide-and-diversify strategy for determining the structural basis of apoptolidin's biological activity. For example, when the C-20/C-21 bond of the apoptolidin derivative of formula (III) is oxidatively cleaved, and the macrocyclic aldehyde is reduced, the cyclic ether of formula (VI) and the δ-lactone of formula (VII) result.

-continued

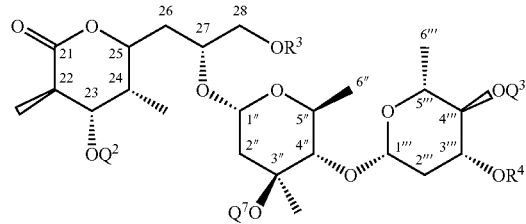

(VII)

The procedure for separating apoptolidin into the structures of formulas (VI) and (VII) is described in Example 6. When the C-19/C-20 diol is activated by formation of the stanylidine acetal, it undergoes a retro-aldol reaction to cleave the C-22/C-23 carbon-carbon bond as shown in formulae (VIII) and (IX)

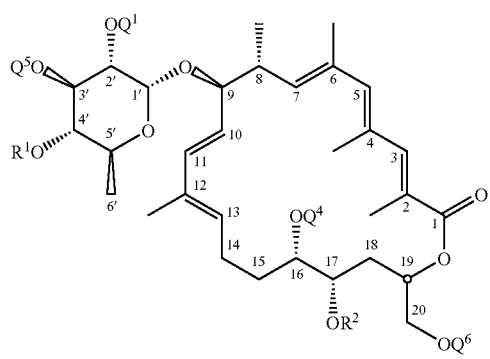

(VI)

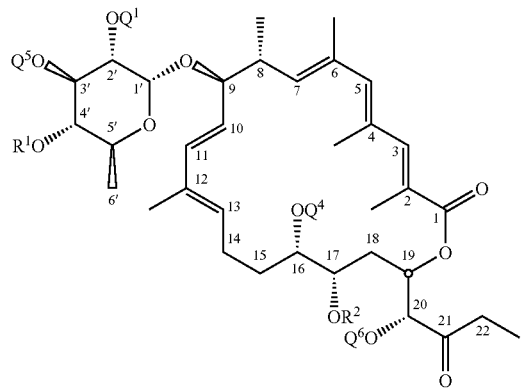

(VIII)

-continued

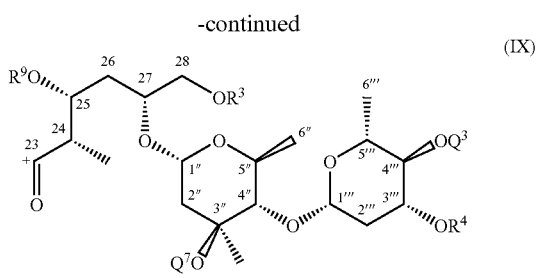

(IX)

wherein R⁹ is selected from H, $C_1$–$C_{12}$ hydrocarbyl, —(CO)—R⁵ wherein R⁵ is $C_1$–$C_{12}$ hydrocarbyl, and hydroxyl-protecting groups.

III. Utility, Testing, and Administration:

As previously mentioned, the compounds of the present invention are useful as therapeutic agents for the treatment of cancer or other disorders responsive to selective apoptosis. The compounds can be administered to a human patient by themselves or in pharmaceutical compositions in which they are mixed with suitable carriers or excipients. Compounds of the invention may also be administered in combination, in which case they may be administered separately, in different dosage forms, or simultaneously, either in one dosage form or in two different dosage forms. Pharmaceutically acceptable dosage forms are described infra.

Representative cancer conditions and cell types against which the compounds of the invention may be useful include melanoma, myeloma, chronic lymphocytic leukemia (CLL), AIDS-related lymphoma, non-Hodgkin's lymphoma, colorectal cancer, renal cancer, prostate cancer, cancers of the head, neck, stomach, esophagus, anus, or cervix, ovarian cancer, breast cancer, peritoneal cancer, and non-small cell lung cancer. A compound of the invention can be administered alone, i.e., in monotherapy, or in combination with one or more other active agents, e.g., other anticancer agents.

In practicing various aspects of the present invention, compounds in accordance with the invention can be tested for a biological activity of interest using any assay protocol that is predictive of activity in vivo.

A useful method for assessing anticancer activities of compounds of the invention involves the multiple-human cancer cell line screening assays run by the National Cancer Institute (e.g., Boyd, "Status of the NCI Preclinical Antitumor Drug Discovery Screen" in *Cancer: Principles and Practice of Oncology Updates*, DeVita et al., eds, pp. 1–12 (1989)). The screening panel, which involves approximately 60 different human cancer cell lines, is a useful indicator of in vivo antitumor activity for a broad variety of tumor types (Grever et al. (1992) *Seminars Oncol.* 19:622; Monks et al. (1991) *J. Natl. Cancer Inst.* 83:757–766), such as leukemia, non-small cell lung, colon, central nervous system (CNS), melanoma, ovarian, renal, prostate, and breast cancers. Antitumor activities can be expressed in terms of $ED_{50}$ (or $GI_{50}$), where $ED_{50}$ is the molar concentration of compound effective to reduce cell growth by 50%. Compounds with lower $ED_{50}$ values tend to have greater anticancer activities than compounds with higher $ED_{50}$ values. Example 7 of U.S. Patent Application Publication No. 2002/0137789, noted above, describes a P388 murine lymphocytic leukemia cell assay that measures the ability of compounds of the invention to inhibit cellular growth.

To study the biological activities of the claimed apoptolidin analogs and derivatives, mitochondrial $F_0F_1$-ATPase inhibition assays were performed; the results of these experiments are set forth in Example 5. Upon the confirmation of a compound's potential activity in vitro, further evaluation is typically conducted in vivo in laboratory animals, for example, by measuring reduction of lung nodule metastases in mice with B16 melanoma (e.g., Schuchter et al, (1991) *Cancer Res.* 51(2):682–687). The efficacy of drug combination chemotherapy can be evaluated, for example, using the human B-CLL xenograft model in mice (e.g., Mohammad et al., (1996) *Leukemia* 10(1): 130–137). Ultimately, the safety and efficacy of compounds of the invention are evaluated in human clinical trials.

Administration of a compound of the invention may be carried out using any appropriate mode of administration. Thus, administration can be, for example, oral, parenteral, transdermal, transmucosal (including rectal and vaginal), sublingual, by inhalation, or via an implanted reservoir in a dosage form. The term "parenteral" as used herein is intended to include subcutaneous, intravenous, and intramuscular injection.

Depending on the intended mode of administration, the pharmaceutical formulation may be a solid, semi-solid or liquid, such as, for example, a tablet, a capsule, a caplet, a liquid, a suspension, an emulsion, a suppository, granules, pellets, beads, a powder, or the like, preferably in unit dosage form suitable for single administration of a precise dosage. Suitable pharmaceutical compositions and dosage forms may be prepared using conventional methods known to those in the field of pharmaceutical formulation and described in the pertinent texts and literature, e.g., in *Remington: The Science and Practice of Pharmacy* (Easton, Pa.: Mack Publishing Co., 1995). For those compounds that are orally active, oral dosage forms are generally preferred, and include tablets, capsules, caplets, solutions, suspensions and syrups, and may also comprise a plurality of granules, beads, powders, or pellets that may or may not be encapsulated. Preferred oral dosage forms are tablets and capsules.

Tablets may be manufactured using standard tablet processing procedures and equipment. Direct compression and granulation techniques are preferred. In addition to the active agent, tablets will generally contain inactive, pharmaceutically acceptable carrier materials such as binders, lubricants, disintegrants, fillers, stabilizers, surfactants, coloring agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose, and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

Oral dosage forms, whether tablets, capsules, caplets, or particulates, may, if desired, be formulated so as to provide for gradual, sustained release of the active agent over an extended time period. Generally, as will be appreciated by those of ordinary skill in the art, sustained release dosage forms are formulated by dispersing the active agent within a matrix of a gradually hydrolyzable material such as a hydrophilic polymer, or by coating a solid, drug-containing dosage form with such a material. Hydrophilic polymers useful for providing a sustained release coating or matrix include, by way of example: cellulosic polymers such as hydroxypropyl cellulose, hydroxyethyl cellulose, hydroxypropyl methyl cellulose, methyl cellulose, ethyl cellulose, cellulose acetate, and carboxymethylcellulose sodium; acrylic acid polymers and copolymers, preferably formed from acrylic acid, methacrylic acid, acrylic acid alkyl esters, methacrylic acid alkyl esters, and the like, e.g. copolymers of acrylic acid, methacrylic acid, methyl acrylate, ethyl acrylate, methyl methacrylate and/or ethyl methacrylate; and vinyl polymers and copolymers such as polyvinyl pyrrolidone, polyvinyl acetate, and ethylene-vinyl acetate copolymer.

Preparations according to this invention for parenteral administration include sterile aqueous and nonaqueous solutions, suspensions, and emulsions. Injectable aqueous solutions contain the active agent in water-soluble form. Examples of nonaqueous solvents or vehicles include fatty oils, such as olive oil and corn oil, synthetic fatty acid esters, such as ethyl oleate or triglycerides, low molecular weight alcohols such as propylene glycol, synthetic hydrophilic polymers such as polyethylene glycol, liposomes, and the like. Parenteral formulations may also contain adjuvants such as solubilizers, preservatives, wetting agents, emulsifiers, dispersants, and stabilizers, and aqueous suspensions may contain substances that increase the viscosity of the suspension, such as sodium carboxymethyl cellulose, sorbitol, and dextran. Injectable formulations are rendered sterile by incorporation of a sterilizing agent, filtration through a bacteria-retaining filter, irradiation, or heat. They can also be manufactured using a sterile injectable medium. The active agent may also be in dried, e.g., lyophilized, form that may be rehydrated with a suitable vehicle immediately prior to administration via injection.

The compounds of the invention may also be administered through the skin using conventional transdermal drug delivery systems, wherein the active agent is contained within a laminated structure that serves as a drug delivery device to be affixed to the skin. In such a structure, the drug composition is contained in a layer, or "reservoir," underlying an upper backing layer. The laminated structure may contain a single reservoir, or it may contain multiple reservoirs. In one embodiment, the reservoir comprises a polymeric matrix of a pharmaceutically acceptable contact adhesive material that serves to affix the system to the skin during drug delivery. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. Transdermal drug delivery systems may in addition contain a skin permeation enhancer.

In addition to the formulations described previously, the compounds may also be formulated as a depot preparation for controlled release of the active agent, preferably sustained release over an extended time period. These sustained release dosage forms are generally administered by implantation (e.g., subcutaneously or intramuscularly or by intramuscular injection).

Although the present compositions will generally be administered orally, parenterally, transdermally, or via an implanted depot, other modes of administration are suitable as well. For example, administration may be rectal or vaginal, preferably using a suppository that contains, in addition to the active agent, excipients such as a suppository wax. Formulations for nasal or sublingual administration are also prepared with standard excipients well known in the art. The pharmaceutical compositions of the invention may also be formulated for inhalation, e.g., as a solution in saline, as a dry powder, or as an aerosol.

It is to be understood that while the invention has been described in conjunction with the preferred specific embodiments thereof, the description above as well as the examples that follow are intended to illustrate and not limit the scope of the invention. Other aspects, advantages, and modifications within the scope of the invention will be apparent to those skilled in the art to which the invention pertains.

All patents, patent applications, journal articles, and other reference cited herein are incorporated by reference in their entireties.

Experimental

Unless noted otherwise, materials were obtained from commercially available sources and used without further purification.

All operations involving moisture-sensitive materials were conducted in oven- and/or flame-dried glassware under an atmosphere of anhydrous nitrogen. Hygroscopic solvents and liquid reagents were transferred using dry Gastigh™ syringes or cannulating needles. In cases where rigorous exclusion of dissolved oxygen was required, solvents were degassed via consecutive freeze, pump, thaw cycles, or inert gas purge.

Nuclear magnetic resonance (NMR) spectra were recorded on either a Varian UNITY INOVA-500, XL400 or a Gemini-300 magnetic resonance spectrometer. $^1$H chemical shifts are given in parts per million ($\delta$) downfield from tetramethylsilane (TMS) using the residual solvent signal ($CHC_3$=$\delta$ 7.27, benzene=$\delta$ 7.15, methanol=$\delta$ 3.30) as internal standard. Proton ($^1$H) NMR information is tabulated in the following format: number of protons, multiplicity (s, singlet; d, doublet; t, triplet; q, quartet; sept, septet, m, multiplet), coupling constant(s) (J) in hertz and, in cases where mixtures are present, assignment as the major or minor isomer, if possible. Proton decoupled $^{13}$C NMR spectra are reported in ppm ($\delta$) relative to residual $CHCl_3$ ($\delta$ 77.25) unless noted otherwise. Deuterated NMR solvents were dried over $\frac{1}{16}$" bead 4 Å molecular sieves.

Flash chromatography was performed using E. Merck silica gel 60 (240–400 mesh) according to the protocol of Still et al. (1978) *J. Org. Chem.* 43:2923. Thin layer chromatography was performed using precoated plates purchased from E. Merck (silica gel 60 PF254, 0.25 mm) that were visualized using either a p-anisaldehyde or Ce(IV) stain. In a typical procedure, 1.0 g cell extract was purified using a 40 cm×2.5 cm flash column of 230–400 mesh normal phase silica eluting with 7% methanol in chloroform where applicable.

Rotating-frame Overhauser Effect Spectroscopy (ROESY) correlations were used in conjunction with an MC conformational search to determine the solution structure of apoptolidin, isoapoptolidin, and derivatives and analogs of same. Calculations performed using the GB/SA water solvation model were performed according to the protocol in Still et al., (1990) *J. Am. Chem. Soc.* 112:6127.

EXAMPLE 1

Structural Characteristics of Isoapoptolidin

Isoapoptolidin, which has a slightly lower $R_f$ on normal phase silica than apoptolidin, was isolated from apoptolidin in crude cell extracts by flash column chromatography. An enriched solution of isoapoptolidin in either chloroform or acetonitrile over several hours at room temperature produced pure isoapoptolidin as white filamentous crystals (mp 134–146° C.). While even very dilute solutions of isoapoptolidin results in crystallization, the presence of apoptolidin in the solution will hinder the crystallization of isoapoptolidin. Mass recovery of apoptolidin and isoapoptolidin from crude cell extracts indicates that the two isomers are present in roughly equal amounts.

The crystals of isoapoptolidin were found unsuitable for X-ray analysis due to a poor aspect ratio and consequently, the structure of isoapoptolidin was determined by analysis of one- and two-dimensional NMR spectra (500 MHz). In deuterated methanol ($CD_3OD$), the chemical shifts of most proton signals in isoapoptolidin remain very similar to those reported for apoptolidin (see, Kim et al., supra). In double quantum filtered correlated spectroscopy (DQF-COSY) experiments, isoapoptolidin and apoptolidin showed the same spin systems; however, the Heteronuclear Multi-Bond Connectivity (HMBC) spectrum of isoapoptolidin, showed a strong correlation between the carbonyl carbon (C-1) and 20-H. Further, the chemical shift of 20-H shifted downfield, from 3.57 ppm in apoptolidin to 4.98 in apoptolidin, suggesting that the 20-H is geminal to the lactone functionality.

The proton ($^1H$ (500 MHz)) and carbon ($^{13}C$ (100 MHz)) NMR data for isoapoptolidin in $CD_3OD$ are summarized in Table 1.

TABLE 1

NMR DATA FOR ISOAPOPTOLIDIN IN $CD_3OD$

| | ISOAPOPTOLIDIN | | APOPTOLIDIN | | ISOAPOPTOLIDIN | | APOPTOLIDIN |
|---|---|---|---|---|---|---|---|
| NO. | $\delta_C$ | $\delta_H$ (J = Hz) | $\delta_H$ | NO. | $\delta_C$ | $\delta_H$ (J = Hz) | $\delta_H$ |
| 1 | 169.92 | | | 2-Me | 13.92 | 2.04 | 2.14 |
| 2 | 124.86 | | | 4-Me | 17.82 | 2.07 | 2.21 |
| 3 | 147.08 | 7.31 | 7.41 | 6-Me | 17.63 | 1.72 (1.0) | 1.97 |
| 4 | 132.76 | | | 8-Me | 18.26 | 1.17 (6.4) | 1.17 |
| 5 | 143.65 | 5.93 | 6.23 | 12-Me | 12.00 | 1.70 | 1.71 |
| 6 | 132.90 | | | 17-OMe | 59.87 | 3.47 | 3.40 |
| 7 | 136.75 | 5.06 (9.1) | 5.27 | 22-Me | 12.13 | 1.03 (6.7) | 1.06 |
| 8 | 39.41 | 2.74 | 2.79 | 24-Me | 5.38 | 0.86 (6.9) | 0.92 |
| 9 | 83.98 | 3.77 (9.0, 9.0) | 3.87 | 28-OMe | 59.48 | 3.35 | 3.30 |
| 10 | 125.77 | 5.26 (9.6, 4.8) | 5.26 | 1' | 96.23 | 4.78 (3.8) | 4.85 |
| 11 | 141.01 | 6.04 (15.8) | 6.21 | 2' | 73.32 | 3.38 (9.8, 3.8) | 3.44 |
| 12 | 134.05 | | | 3' | 74.92 | 3.71 | 3.76 |
| 13 | 133.80 | 5.48 (9.6, 4.8) | 5.71 | 4' | 87.53 | 2.70 (9.0) | 2.76 |
| 14α | 25.49 | 1.93 | 2.09 | 5' | 68.05 | 3.73 | 3.78 |
| 14β | | 2.48 | 2.50 | 6' | 18.38 | 1.22 (6.2) | 1.29 |
| 15α | 33.37 | 1.24 | 1.44 | 4'-OMe | 61.01 | 3.56 | 3.61 |
| 15β | | 1.39 | 1.52 | 1" | 99.88 | 5.05 (4.1) | 4.97 |
| 16 | 73.10 | 3.51 (10.3, 5.0, 2.3) | 3.47 | 2"α | 45.29 | 2.01 | 1.96 |
| 17 | 81.89 | 3.36 | 2.75 | 2"β | | 1.77 | 1.84 |
| 18α | 35.05 | 1.36 | 1.78 | 3" | 73.67 | | |
| 18β | | 1.84 | 2.20 | 4" | 85.91 | 3.32 | 3.37 |
| 19 | 67.44 | 4.41 (11.3, 3.7, 2.1) | 5.32 | 5" | 68.62 | 3.73 | 3.70 |
| 20 | 74.13 | 4.98 (3.7) | 3.57 | 6" | 18.35 | 1.22 (6.2) | 1.25 |
| 21 | 103.27 | | | 3"-Me | 22.76 | 1.34 | 1.36 |
| 22 | 36.79 | 1.77 | 2.08 | 1'" | 101.91 | 4.82 (9.7, 1.8) | 4.86 |
| 23 | 73.20 | 3.72 | 3.76 | 2'"α | 37.51 | 2.43 (12.3, 5.0, 1.8) | 2.47 |
| 24 | 40.52 | 1.74 | 1.76 | 2'"β | | 1.28 | 1.32 |
| 25 | 68.17 | 4.21 (10.3, 2.5, 2.0) | 3.99 | 3'" | 81.98 | 3.16 (11.6, 9.0, 5.0) | 3.21 |
| 26α | 36.82 | 1.76 | 1.62 | 4'" | 77.12 | 2.95 (9.0, 9.0) | 3.01 |
| 26β | | 1.53 | 1.49 | 5'" | 73.45 | 3.19 | 3.24 |

TABLE 1-continued

NMR DATA FOR ISOAPOPTOLIDIN IN CD₃OD

| ISOAPOPTOLIDIN | | APOPTOLIDIN | ISOAPOPTOLIDIN | | APOPTOLIDIN |
|---|---|---|---|---|---|---|---|
| NO. | $\delta_C$ | $\delta_H$ (J = Hz) | $\delta_H$ | NO. | $\delta_C$ | $\delta_H$ (J = Hz) | $\delta_H$ |
| 27 | 76.24 | (14.7, 10.7, 3.0)<br>3.82 | 3.48 | 6''' | 18.87 | 1.27<br>(6.2) | 1.31 |
| 28 | 77.07 | 3.44 | 3.36 | 3'''-OMe | 57.32 | 3.42 | 3.46 |

The conformation of the isoapoptolidin ring was determined by way of ROESY correlations. Specifically, strong ROESY correlations were observed between 1,3-diaxial substituents on the C-21 to C-25 cyclic hemiketal in isoapoptolidin, indicating that the ring in the C-21 to C-25 puranyl moiety is in a chairlike conformation, and ROESY correlations were observed from 20-H to 22-H and 22-Me-H₃, indicating that C-20 is equatorial on the ring. Using the coupling constant data for the anomeric proton signals (Table 1), it was determined that the stereochemistry of the glycosidic bonds in isoapoptolidin is the same as in apoptolidin. The geometry of the olefins in isoapoptolidin were all determined to be in the (E) geometry through high field carbon shift for the allylic methyl signals and the large vicinal coupling constant across the C-10/C11 double bond; these findings were confirmed via ROESY correlations.

ROESY correlations were also used to determine the solution conformation of isoapoptolidin. Of 51 ROESY correlations for the C-1 to C-26 portion of isoapoptolidin, 23 were found nontrivial and applied in subsequent analyses. Strong ROESY correlations were observed between 3-H and 5-H and between 5-H and 7-H, indicating that the three methyl groups on the triene line of isoapoptolidin lie on the same face of the macroline as they do in apoptolidin. It was also noted that isoapoptolidin had transannular correlations between 3-H and both 18-H$_\beta$ and 15-H$_\beta$. The hypochromic shift in the enoate chromophore from a $\lambda_{max}$ of 319 nm in apoptolidin to 304 nm in isoapoptolidin, along with a decrease in the extinction coefficient for this absorption, from 22 800 in apoptolidin to 19 400 in isoapoptolidin, suggests a decrease in the degree of conjugation of the triene system in isoapoptolidin relative to apoptolidin.

Also observed was a high chemical shift of 19-H in isoapoptolidin, which is probably attributable to a new hydrogen bond between the C-19 alcohol and the C-25 oxygen. Significant ROESY correlations between the 20-H and the 22-H proton suggest an arrangement of the C-20/C-21 torsion that would favor this hydrogen bond. A representative structure from the conformational search is depicted in FIG. 1 and is fully consistent with date from the ROESY experiment.

EXAMPLE 2

Kinetic Parameters of Isoapoptolidin

To study the kinetic parameters of isoapoptolidin, the conversion between apoptolidin and isoapoptolidin under biological assay and chemical isolation conditions was observed. Apoptolidin has been found to be stable for up to three months at −20° C. when dissolved in chloroform or methylene chloride. During this time, no conversion to isoapoptolidin is observed, either by NMR or HPLC. Similarly, isoapoptolidin is stable as a solution in methanol at −20° C. for up to six months. In contrast, a dilute aqueous solution of apoptolidin at ambient temperature can be observed to convert to isoapoptolidin when monitored by HPLC or UV-vis as will a dilute aqueous solution of isoapoptolidin at ambient temperature will convert to apoptolidin when monitored by HPLC and UV-vis. Given that the conversion between apoptolidin and isoapoptolidin goes in both directions, it is likely that these two compounds are in equilibrium.

Figure 2:
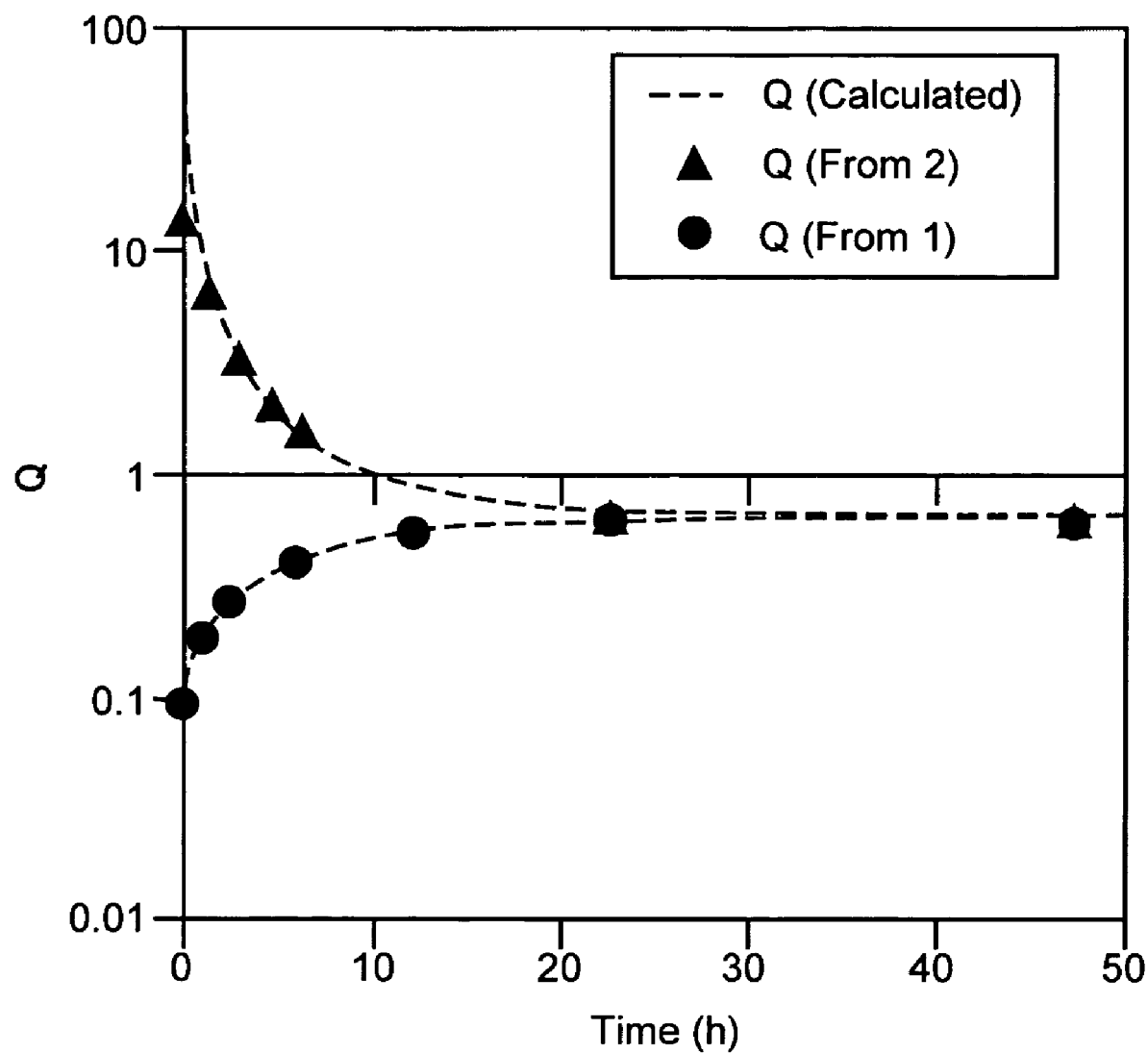
FIG. 2 shows a graph of kinetics toward equilibrium for the conversion of isoapoptolidin to apoptolidin and for the conversion of apoptolidin to isoapoptolidin in aqueous solution where Q=[2]/[1].

To measure the kinetic parameters of apoptolidin and isoapoptolidin, solutions of both compounds in PBS (Dulbecco's phosphate buffered saline) were prepared and incubated at 37° C. in sealed reaction vessels. Periodically, the components present in the solutions were quantified using reverse-phase HPLC. Baseline separation was achieved using a 150×4.6 mm C18/5µ column eluting with a water/acetonitrile gradient from 40% to 90% over 30 min. After normalization for the difference in extinction coefficients ($\lambda_{obs}$=254 nm), these values were plotted and the rate constants $k_1$ and $k_{-1}$ were extracted by fitting the data to the integrated rate expression for a simple equilibrium. The kinetic parameters for apoptolidin and isoapoptolidin equilibrium over time in PBS at 37° C. (where Q(t)=[2]/[1]) are set forth in Table 2. The relative amounts of apoptolidin and isoapoptolidin at various time points are plotted in FIG. 2.

TABLE 2

KINETIC PARAMETERS FOR
APOPTOLIDIN-ISOAPOPTOLIDIN EQUILIBRIUM $$\text{APOPTOLIDIN} \underset{k_{-1}}{\overset{k_1}{\rightleftarrows}} \text{ISOAPOPTOLIDIN}$$

| | Q(t) = 0 at t = 0 | Q(t) = ∞ at t = 0 |
|---|---|---|
| $k_1$ | 0.0656 h⁻¹ | 0.0626 h⁻¹ |
| $k_{-1}$ | 0.106 h⁻¹ | 0.0982 h⁻¹ |
| $K_{eq}$ | 0.0616 | 0.638 |

Q(t) = [2]/[1] at time t.

The similar rate parameters derived from solutions starting with either isoapoptolidin or apoptolidin suggests the absence of any long-lived intermediate structure in the interconversion between the two molecules. Further, the value of $k_1$ suggests that under conditions of most cell-based assays, a significant conversion of apoptolidin to isoapoptolidin will occur within several hours. These findings indicate that the presence of isoapoptolidin must be taken into account when interpreting the results of cell-based assays.

EXAMPLE 3

Selective Functionalization of the Eight Hydroxyl Groups of Apoptolidin

To study the structure-activity relationship of apoptolidin and its analogs, the eight hydroxyl functionalities of apoptolidin were substituted to produce apoptolidin derivatives. The hydroxyl groups were selected for this study because of their potential role as pharmacophoric hydrogen bond donors and acceptors.

to both install and remove with difficulty. By altering the number of equivalents of triethylsilyl triflate used in the protection step, each of the corresponding silyl ethers of apoptolidin identified as compounds 4–8 in Table 3 were selectively formed. Careful acetylation of the silyl ethers of compounds 4–8 produced compounds 9–13 of Table 3, respectively. Finally, silyl deprotection of each derivative with buffered hydrogen fluoride (HF) produced compounds 14–18 of Table 3. The functional groups referenced in Table 3 correspond to the groups shown in the compound of formula (II).

TABLE 3

FUNCTIONAL SELECTION OF HYDROXYL GROUPS OF APOPTOLIDIN

| POSITION OF OH GROUP | REAGENT | CMPD NO. | FUNCTIONAL GROUPS | FINAL PRODUCT |
|---|---|---|---|---|
| C-21 | MeOH Amberlyst-15 | 1 | $Q^1 = Q^2 = Q^3 = Q^4 = Q^5 = Q^6 = Q^7 = H, Q^8 = CH_3$ | KETAL |
| C-2' | $Piv_2O$ pyr, DMAP | 2 | $Q^1 = Piv, Q^2 = Q^3 = Q^4 = Q^5 = Q^6 = Q^7 = Q^8 = H$ | ESTER |
| C-2'/C-3' | $Bu_2SnO$, 4Å M.S. then BzCl | 3 | $Q^1 = Bz, Q^2 = Q^3 = Q^4 = Q^5 = Q^6 = Q^7 = Q^8 = H$ | BENZOATE |
| REMAINING HYDROXYL GROUPS C-16 C-20 C-23 C-3" C-4" | TESOTf, DCM, THF, pyr or 2,6-lut | 4 | $Q^1 = TES, Q^2 = Q^3 = Q^4 = Q^5 = Q^6 = Q^7 = Q^8 = H$ | SILYL ETHERS |
| | | 5 | $Q^1 = Q^2 = TES, Q^3 = Q^4 = Q^5 = Q^6 = Q^7 = Q^8 = H$ | |
| | | 6 | $Q^1 = Q^2 = Q^3 = TES, Q^4 = Q^5 = Q^6 = Q^7 = Q^8 = H$ | |
| | | 7 | $Q^1 = Q^2 = Q^3 = Q^4 = TES, Q^5 = Q^6 = Q^7 = Q^8 = H$ | |
| | | 8 | $Q^1 = Q^2 = Q^3 = Q^4 = Q^5 = TES, Q^6 = Q^7 = Q^8 = H$ | |
| | $Ac_2O$, DCM, pyr, DMAP | 9 | $Q^1 = TES, Q^2 = Q^3 = Ac, Q^4 = Q^5 = Q^6 = Q^7 = Q^8 = H$ | ACETYLATED SILYL ETHERS |
| | | 10 | $Q^1 = Q^2 = TES, Q^3 = Ac, Q^4 = Q^5 = Q^6 = Q^7 = Q^8 = H$ | |
| | | 11 | $Q^1 = Q^2 = Q^3 = TES, Q^4 = Ac, Q^5 = Q^6 = Q^7 = Q^8 = H$ | |
| | | 12 | $Q^1 = Q^2 = Q^3 = Q^4 = TES, Q^5 = Ac, Q^6 = Q^7 = Q^8 = H$ | |
| | | 13 | $Q^1 = Q^2 = Q^3 = Q^4 = Q^5 = TES, Q^6 = Ac, Q^7 = Q^8 = H$ | |
| | HF-pyr, pyr, THF | 14 | $Q^1 = H, Q^2 = Q^3 = Ac, Q^4 = Q^5 = Q^6 = Q^7 = Q^8 = H$ | ACETATES |
| | | 15 | $Q^1 = Q^2 = H, Q^3 = Ac, R^4 = R^5 = Q^6 = Q^7 = Q^8 = H$ | |
| | | 16 | $Q^1 = Q^2 = Q^3 = H, Q^4 = Ac, Q^5 = Q^6 = Q^7 = Q^8 = H$ | |
| | | 17 | $Q^1 = Q^2 = Q^3 = Q^4 = H, Q^5 = Ac, Q^6 = Q^7 = Q^8 = H$ | |
| | | 18 | $Q^1 = Q^2 = Q^3 = Q^4 = Q^5 = H, Q^6 = Ac, Q^7 = Q^8 = H$ | |

In Table 3, the abbreviations used are as follows:
Ac = acetyl;
$Ac_2O$ = acetyl acetone;
DCM = dichloromethane;
DMAP = dimethylaminopyridine;
THF = tetrahydrofuran;
TES = triethylsilyl;
Bz = benzoyl; and
Piv = pivaloyl.

Figure 3:
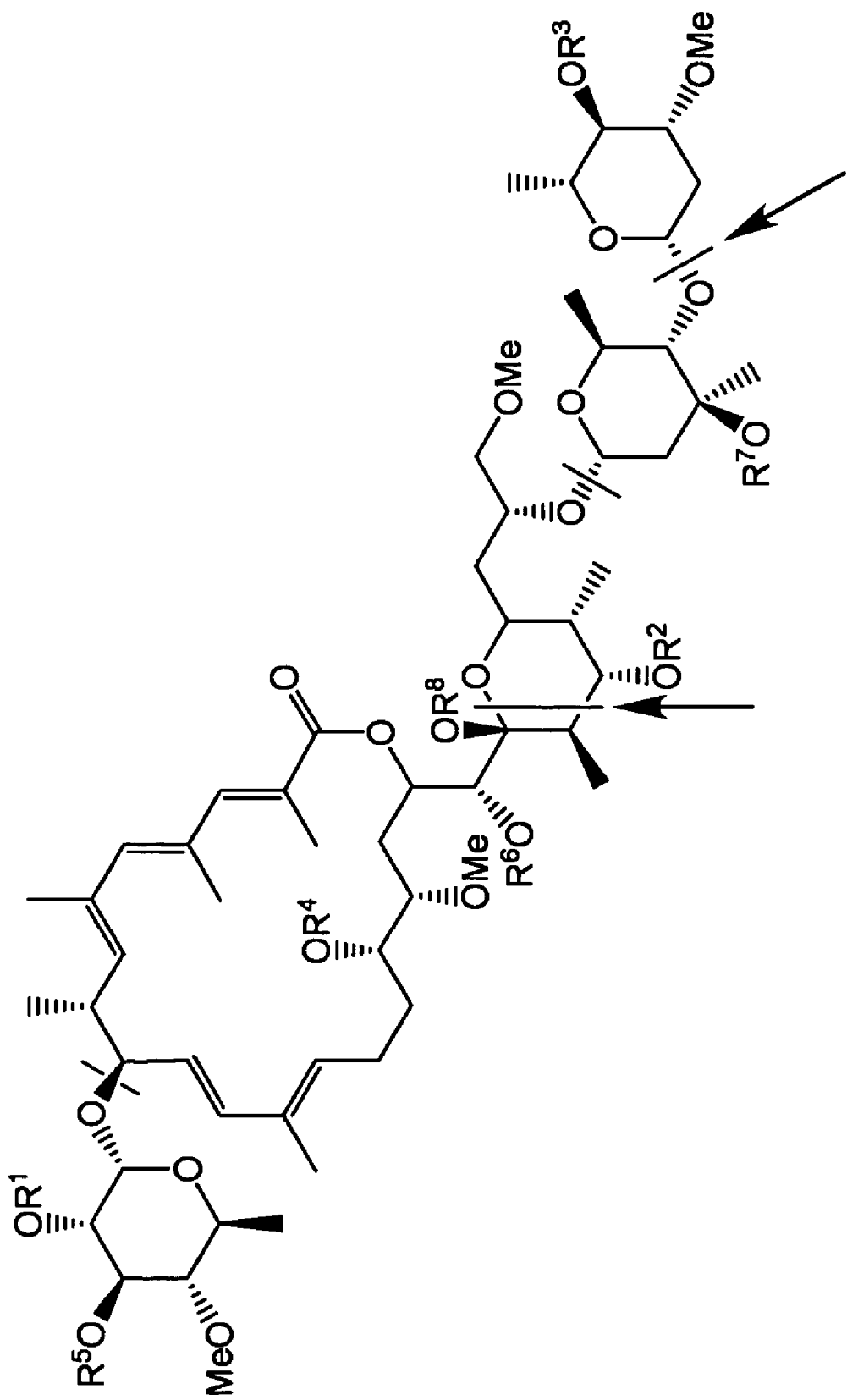
FIG. 3 shows some common (+)ESIMS fragmentation sites for derivatives of apoptolidin.

The functional selection of the eight hydroxyl groups of apoptolidin is shown schematically in Table 3. Of the eight hydroxyl groups of apoptolidin, the sole cyclic hemi-ketal C-21 was selectively derivatized by treatment with Amberlyst™-15 sulfonic acid resin in methanol to result in a ketal in 80% yield (compound 1). The hydroxyl at C-2' was found to be the most reactive toward acylation and thus was selectively esterified by using pivaloyl anhydride ("$Piv_2O$"; compound 2). The C-2'/C-3' diol was activated through formation of a dibutylstannylidene acetal followed by treatment with benzoyl chloride to produce a C-2' benzoate (compound 3). The remaining hydroxyl groups were selectively functionalized by using a strategy of progressive selective protection with triethylsilyl ether, followed by acetylation and deprotection. For protection, triethylsilyl ether was found to be most effective as it was easily installed with good chemoselectivity and removed under mild conditions. By contrast, tert-butyldimethylsilyl ether was found The location of the acetyl group in the acetates at compounds 14–18 was determined by analysis of their proton chemical shift assignments based on 2D-NMR experiments. The downfield chemical shift of the proton geminal to the newly formed ester was used to identify the site of derivatization. Proton chemical shifts also served to confirm that macrolide ring expansion did not occur. The location of the silyl ethers in compounds 4–13 was inferred by the identities of compounds 14–18. When analyzed by tandem mass spectrometry, apoptolidin and its derivatives fragmented in a consistent way that allowed for a cross-check of the NMR assignments, and thus served as an independent confirmation of structure. FIG. 3 shows the fragmentation sites for the apoptolidin derivatives produced herein. On the basis of the fragmentation patterns of compounds 9–13, it was concluded that silyl transfer did not occur during the acetylation of compounds 4–8.

EXAMPLE 4

Functionalization of the C-20 Hydroxyl Group of Apoptolidin

To determine whether apoptolidin or isoapoptolidin is primarily responsible for apoptosis, the C-20 alcohol of apoptolidin was functionalized in order to prepare an apoptolidin derivative that does not isomerize to isoapoptolidin.

The functional selection of the C-20 alcohol of apoptolidin is shown schematically in Table 4. For this experiment, the penta-(triethylsilyl)-protected apoptolidin of Table 3 (compound 8) was reacted with Meerwein's salt in the presence of 2,6-di-tert-butyl-4-methylpyridine to produce the C-20 methyl-ether identified as compound 19 in Table 4. Compound 19 was subsequently deprotected to yield the apoptolidin derivative identified as compound 20 in Table 4. The location of the methyl ether was confirmed by observation of the strong HMBC correlations between C-20 and the C-20 methoxy protons.

TABLE 4

FUNCTIONAL SELECTION OF THE
C-20 ALCOHOL OF APOPTOLIDIN

| CMPD NO. | FUNCTIONAL GROUPS | FINAL PRODUCT | REAGENT |
|---|---|---|---|
| 8 | $Q^1 = Q^2 = Q^3 = Q^4 = Q^5 = $ TES, $Q^6 = Q^7 = Q^8 = $ H | SILYL ETHER | |
| 19 | $Q^1 = Q^2 = Q^3 = Q^4 = Q^5 = $ TES $Q^6 = $ Me, $Q^7 = Q^8 = $ H | METHYL ETHER | Me$_3$OBF$_4$, DCM, 2,6-di-tert-butyl-4-methylpyridine |
| 20 | $Q^1 = Q^2 = Q^3 = Q^4 = Q^5 = Q^7 = Q^8 = $ H, $Q^6 = $ Me | METHYL ETHER | HF-pyr, pyr, THF |

The stability of compound 20 was studied in PBS, under the same conditions described in Example 1 that were found to promote the isomerization of isoapoptolidin to apoptolidin. For compound 20, the macrolactone could not undergo ring expansion; however, this compound was found to partially convert to a second isomeric compound over a period of several hours, as observed by liquid chromatography and mass spectrometry (LC-MS). Similarly, the C-20 acetate derivative (compound 18) was also found to be unstable under these conditions, producing several new compounds over a five hour period. This experiment leads to the conclusion that while derivatization of apoptolidin at C-20 blocks isomerization to isoapoptolidin, the resulting derivatives (compounds 18 and 20) undergo other transformations.

EXAMPLE 5

F$_0$F$_1$-ATPase Studies

The ability of isoapoptolidin and the apoptolidin derivatives described in Examples 3 and 4 to inhibit F$_0$F$_1$-ATPase in isolated yeast mitochondria was studied. The F$_0$F$_1$-ATPase assay is a rapid 20 minute cell-free assay. The short duration of the assay ensures that isomerization of isoapoptolidin to apoptolidin is minimal and the cell-free nature of the assay ensures that the acetate derivatives of apoptolidin will be stable and not subject to hydrolysis.

To test the ability of isoapoptolidin to inhibit F$_0$F$_1$-ATPase activity, solutions of isoapoptolidin and apoptolidin including all assay components were analyzed for isomerization. After 20 minutes at 37° C., less than 12% conversion was detected.

To test the ability of apoptolidin derivatives to inhibit F$_0$F$_1$-ATPase activity, compound 16 from Table 3 was exposed to all of the assay components for up to 24 hours. The assay solution was then analyzed for hydrolysis products using Electrospray Ionization Mass Spectrometry (ES-IMS), and no hydrolysis was detected.

The data for the F$_0$F$_1$-ATPase inhibition assay for apoptolidin, isoapoptolidin, and the apoptolidin derivatives identified as compounds 1, 3, 14, 15, 16, 17, 18, and 20 above is provided in Table 5. The results of the assay show that while isoapoptolidin has reduced F$_0$F$_1$-ATPase inhibitory activity over apoptolidin, many of the apoptolidin derivatives show F$_0$F$_1$-ATPase inhibitory activity similar to that of apoptolidin.

TABLE 5

F$_0$F$_1$-ASSAY FOR APOPTOLIDIN, ISOAPOPTOLIDIN,
AND APOPTOLIDIN DERIVATIVES

| | IC$_{50}$ (μM) |
|---|---|
| APOPTOLIDIN | 0.7 ± 0.5 |
| ISOAPOPTOLIDIN | 17 ± 5.0 |
| COMPOUND 1 | 2.3 ± 0.5 |
| COMPOUND 3 | 0.3 ± 0.5 |
| COMPOUND 14 | 0.4 ± 0.5 |
| COMPOUND 15 | 0.8 ± 0.5 |
| COMPOUND 16 | 0.8 ± 0.5 |
| COMPOUND 17 | 0.4 ± 0.5 |
| COMPOUND 18 | 1.1 ± 0.5 |
| COMPOUND 20 | 2.8 ± 0.5 |

EXAMPLE 6

Oxidative Cleavage of Apoptolidin

In a preliminary experiment to cleave apoptolidin, the molecule was treated with sodium periodate in a 1:1 mixture of methanol and water; this reaction yielded a considerable amount of lactone and trace amounts of the macrolide fragment. After investigating various protection strategies and oxidant screenings, it was found that reaction of pentatriethylsilyl protected apoptolidin (Table 4, compound 8) with lead tetraacetate under mild anhydrous conditions results in the rapid cleavage of apoptolidin at the C-20/C-21 bond and yields excellent quantities of lactone (87%) and aldehyde (89%). Referring to the formulas (V) and (VI), the resulting compounds had the following scheme:

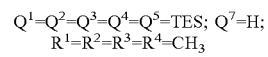

While the C-19/C-20 bond of formula (V) shows an alcohol, the moiety at C-20 of the resulting aldehyde was CHO. To evaluate the stabilities and activities of the derivatives, the fully protected macrocyclic aldehyde was smoothly reduced using sodium borohydride in THF to produce a primary alcohol having the following scheme:

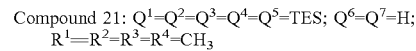

The macrocyclic alcohol was fully desilyated using buffered HF/pyridine to produce a compound with the following scheme:

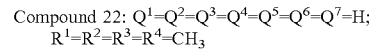

The desilylated macrocyclic alcohol did not isomerize during the desilylation process but slowly isomerized to its ring expanded isomer in basic $CD_3OD$ as determined by LCMS and NMR. To prevent ring expansion, the primary alcohol may be efficiently converted to a methyl ether or benzoate ester by way of treatment with Meerwein's salt or benzoyl anhydride followed by deprotection, under this procedure, the following macrocycles resulted, respectively:

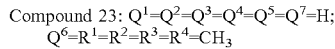

Compound 23: $Q^1=Q^2=Q^3=Q^4=Q^5=Q^7=H$; $Q^6=R^1=R^2=R^3=R^4=CH_3$

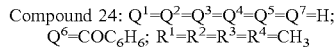

Compound 24: $Q^1=Q^2=Q^3=Q^4=Q^5=Q^7=H$; $Q^6=COC_6H_5$; $R^1=R^2=R^3=R^4=CH_3$ Under the conditions of these transformation, acyl migration was not observed.

The functionalized macrolide and δ-lactone fragments were assayed for inhibitory activity against mitochondrial $F_0F_1$-ATPase. While the δ-lactone fragment had greatly reduced potency as compared with apoptolidin, the macrolide fragments (compounds 21–24) retained significant activity in the assay. The results of the $F_0F_1$-ATPase assay for the apoptolidin oxidative cleavage products are set forth in Table 6.

TABLE 6

$F_0F_1$-ASSAY FOR APOPTOLIDIN OXIDATIVE CLEAVAGE PRODUCTS

| | $IC_{50}$ (µM) |
|---|---|
| APOPTOLIDIN | 0.7 ± 0.5 |
| ISOAPOPTOLIDIN | 17 ± 5.0 |
| COMPOUND 8 | 190 ± 50.0 |
| COMPOUNDS 21 | 13.0 ± 5.0 |
| COMPOUND 22 | 16 ± 5.0 |
| COMPOUND 23 | 32 ± 5.0 |
| COMPOUND 24 | 34 ± 5.0 |

Compound 21 and compound 22 (the methyl ester) were both found to have a potency comparable to isoapoptolidin whereas compound 23 (the benzoate derivative) and compound 24 were found to be less active than compounds 21 and 22 as well as apoptolidin and isoapoptolidin. These results are consistent with the observation of decreased potency upon functionalization of the C-20 bond of apoptolidin, either as an acetate or a methyl ester.

We claim:

1. A functionalized isoapoptolidin compound consisting essentially of an isoapoptolidin core or a stereoisomer thereof, in which:s (a) at least one hydroxyl group in the isoapoptolidin core is replaced with a substituent selected from $C_1$–$C_{24}$ hydrocarbyloxy, $C_2$–$C_{25}$ acyloxy, $C_2$–$C_{25}$ haloacyloxy $C_2$–$C_{25}$ thioacyloxy, $C_2$–$C_{25}$ thiohaloacyloxy, $C_2$–$C_{25}$ carbonato, halogenated $C_2$–$C_{25}$ carbonato, $C_2$–$C_{25}$ thiocarbonato, halogenated $C_2$–$C_{25}$ thiocarbonato, carbamoyloxy, N—($C_1$–$C_{24}$ hydrocarbyl)-substituted carbamoyloxy, N,N-di($C_1$–$C_{24}$ hydrocarbyl)-substituted carbamoyloxy, thiocarbamoyloxy, N—($C_1$–$C_{24}$ hydrocarbyl)-substituted thiocarbamoyloxy, N,N-di($C_1$–$C_{24}$ hydrocarbyl)-substituted thiocarbamoyloxy, sulfamoyloxy, N—($C_1$–$C_{24}$ hydrocarbyl)-substituted sulfamoyloxy, N,N-di($C_1$–$C_{24}$ hydrocarbyl)-substituted sulfamoyloxy, and protected hydroxyl groups;

(b) at least one 1,3-diene functionality in the isoapoptolidin core is replaced by the product of a Diels-Alder reaction with a dienophile;

(c) at least one carbon-carbon double bond in the isoapoptolidin core is replaced with a carbon-carbon single bond; and/or (d) at least one 1,2-diol functionality in the isoapoptolidin core is replaced with a cyclic ether.

2. The functionalized isoapoptolidin compound of claim 1, in which at least one hydroxyl group in the isoapoptolidin core is replaced with a substituent selected from $C_1$–$C_{24}$ hydrocarbyloxy, $C_2$–$C_{25}$ acyloxy, $C_2$–$C_{25}$ haloacyloxy $C_2$–$C_{25}$ thioacyloxy, $C_2$–$C_{25}$ thiohaloacyloxy, $C_2$–$C_{25}$ carbonato, halogenated $C_2$–$C_{25}$ carbonato, $C_2$–$C_{25}$ thiocarbonato, halogenated $C_2$–$C_{25}$ thiocarbonato, carbamoyloxy, N—($C_1$–$C_{24}$ hydrocarbyl)-substituted carbamoyloxy, N,N-di($C_1$–$C_{24}$ hydrocarbyl)-substituted carbamoyloxy, thiocarbamoyloxy, N—($C_1$–$C_{24}$ hydrocarbyl)-substituted thiocarbamoyloxy, N,N-di($C_1$–$C_{24}$ hydrocarbyl)-substituted thiocarbamoyloxy, sulfamoyloxy, N—($C_1$–$C_{24}$ hydrocarbyl)-substituted sulfamoyloxy, N,N-di($C_1$–$C_{24}$ hydrocarbyl)-substituted sulfamoyloxy, and protected hydroxyl groups.

3. The functionalized isoapoptolidin compound of claim 2, wherein the substituent is selected from $C_1$–$C_{12}$ hydrocarbyloxy, $C_2$–$C_{13}$ acyloxy, $C_2$–$C_{13}$ haloacyloxy $C_2C_{13}$ thioacyloxy, $C_2$–$C_{25}$ thiohaloacyloxy, $C_2$–$C_{13}$ carbonato, halogenated $C_2$–$C_{13}$ carbonato, $C_2$–$C_{13}$ thiocarbonato, halogenated $C_2$–$C_{13}$ thiocarbonato, carbamoyloxy, N—($C_1$–$C_{12}$ hydrocarbyl)-substituted carbamoyloxy, N,N-di($C_1$–$C_{12}$ hydrocarbyl)-substituted carbamoyloxy, thiocarbamoyloxy, N—($C_1$–$C_{12}$ hydrocarbyl)-substituted thiocarbamoyloxy, N,N-di($C_1$–$C_{12}$ hydrocarbyl)-substituted thiocarbamoyloxy, sulfamoyloxy, N—($C_1$–$C_{12}$ hydrocarbyl)-substituted sulfamoyloxy, N,N-di($C_1$–$C_{12}$ hydrocarbyl)-substituted sulfamoyloxy, ($C_1$–$C_6$ alkoxy)methyl ether, ($C_1$–$C_6$ alkylthio) methyl ether, and tri($C_1$–$C_{12}$ hydrocarbyl)-substituted silyloxy.

4. The functionalized isoapoptolidin compound of claim 3, wherein the substituent is selected from $C_1$–$C_{12}$ hydrocarbyloxy, $C_2$–$C_{13}$ acyloxy, and tri($C_1$–$C_{12}$ hydrocarbyl)-substituted silyloxy.

5. A compound having the structure of formula (II)

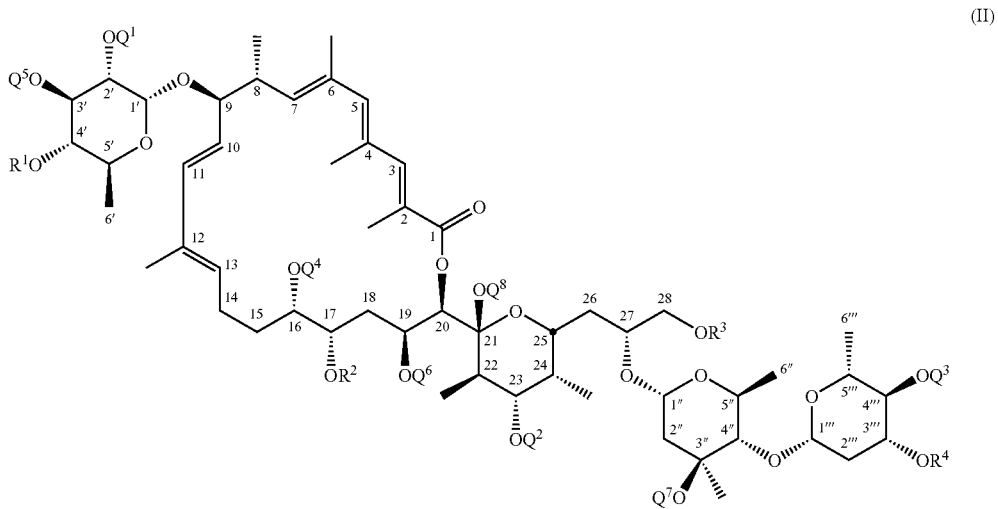

wherein:
  $Q^1$, $Q^2$, $Q^3$, $Q^4$, $Q^5$, $Q^6$, $Q^7$, and $Q^8$ are independently selected from H, $C_1$–$C_{12}$ hydrocarbyl, acyl of the formula —(CO)—$R^5$ in which $R^5$ is $C_1$–$C_{12}$ hydrocarbyl, and hydroxyl-protecting groups; and
  $R^1$, $R^2$, $R^3$, and $R^4$ are $C_1$–$C_{12}$ alkyl or H, or a stereoisomer thereof.

6. The compound of claim 5, having the stereoisomeric configuration of formula (I).

7. The compound of claim 5, wherein:
  $Q^1$, $Q^2$, $Q^3$, $Q^4$, $Q^5$, $Q^6$, $Q^7$, and $Q^8$ are independently selected from H, $C_1$–$C_6$ hydrocarbyl, —(CO)—$R^5$ wherein $R^5$ is $C_1$–$C_6$ hydrocarbyl, and —Si($R^6R^7R^8$) wherein $R^6$, $R^7$, and $R^8$ are $C_1$–$C_6$ hydrocarbyl; and
  $R^1$, $R^2$, $R^3$, and $R^4$ are $C_1$–$C_4$ alkyl.

8. The compound of claim 7, wherein:
  $Q^1$, $Q^2$, $Q^3$, $Q^4$, $Q^5$, $Q^6$, $Q^7$, and $Q^8$ are independently selected from H, $C_1$–$C_6$ alkyl, —(CO)—$R^5$ wherein $R^5$ is $C_1$–$C_6$ alkyl, and —Si($R^6R^7R^8$) wherein $R^6$, $R^7$, and $R^8$ are all methyl or all ethyl; and
  $R^1$, $R^2$, $R^3$, and $R^4$ are methyl.

9. The compound of claim 6, wherein:
  $Q^1$, $Q^2$, $Q^3$, $Q^4$, $Q^5$, $Q^6$, $Q^7$, and $Q^8$ are independently selected from H, $C_1$–$C_6$ hydrocarbyl, —(CO)—$R^5$ wherein $R^5$ is $C_1$–$C_6$ hydrocarbyl, and —Si($R^6R^7R^8$) wherein $R^6$, $R^7$, and $R^8$ are $C_1$–$C_6$ hydrocarbyl; and
  $R^1$, $R^2$, $R^3$, and $R^4$ are $C_1$–$C_4$ alkyl.

10. The compound of claim 9, wherein:
  $Q^1$, $Q^2$, $Q^3$, $Q^4$, $Q^5$, $Q^6$, $Q^7$, and $Q^8$ are independently selected from H, $C_1$–$C^6$ alkyl, —(CO)—$R^5$ wherein $R^5$ is $C_1$–$C_6$ alkyl, and —Si($R^6R^7R^8$) wherein $R^6$, $R^7$, and $R^8$ are all methyl or all ethyl; and
  $R^1$, $R^2$, $R^3$, and $R^4$ are methyl.

11. The compound of claim 5, wherein:
  $Q^1$ is —(CO)—$R^5$ and $Q^2$, $Q^3$, $Q^4$, $Q^5$, $Q^6$, $Q^7$, and $Q^8$ are H;
  $Q^2$ and $Q^3$ are —(CO)—$R^5$ and $Q^1$, $Q^4$, $Q^5$, $Q^6$, $Q^7$, and $Q^8$ are H;
  $Q^3$ is —(CO)—$R^5$ and $Q^1$, $Q^2$, $Q^4$, $Q^5$, $Q^6$, $Q^7$, and $Q^8$ are H;
  $Q^4$ is —(CO)—$R^5$ and $Q^1$, $Q^2$, $Q^3$, $Q^5$, $Q^6$, $Q^7$, and $Q^8$ are H;
  $Q^5$ is —(CO)—$R^5$ and $Q^1$, $Q^2$, $Q^3$, $Q^4$, $Q^6$, $Q^7$, and $Q^8$ are H;
  $Q^6$ is —(CO)—$R^5$ and $Q^1$, $Q^2$, $Q^3$, $Q^4$, $Q^5$, $Q^7$, and $Q^8$ are H;
  $Q^6$ is $C_1$–$C_6$ alkyl and $Q^1$, $Q^2$, $Q^3$, $Q^4$, $Q^5$, $Q^7$, and $Q^8$ are H; or
  $Q^8$ is $C_1$–$C_6$ alkyl and $Q^1$, $Q^2$, $Q^3$, $Q^4$, $Q^5$, $Q^6$, and $Q^7$ are H.

12. The compound of claim 11, wherein:
  $Q^1$ is benzoyl and $Q^2$, $Q^3$, $Q^4$, $Q^5$, $Q^6$, $Q^7$, and $Q^8$ are H;
  $Q^2$ and $Q^3$ are acetyl and $Q^1$, $Q^4$, $Q^5$, $Q^6$, $Q^7$, and $Q^8$ are H;
  $Q^3$ is acetyl and $Q^1$, $Q^2$, $Q^4$, $Q^5$, $Q^6$, $Q^7$, and $Q^8$ are H;
  $Q^4$ is acetyl and $Q^1$, $Q^2$, $Q^3$, $Q^5$, $Q^6$, $Q^7$, and $Q^8$ are H;
  $Q^5$ is acetyl and $Q^1$, $Q^2$, $Q^3$, $Q^4$, $Q^6$, $Q^7$, and $Q^8$ are H;
  $Q^6$ is acetyl and $Q^1$, $Q^2$, $Q^3$, $Q^4$, $Q^5$, $Q^7$, and $Q^8$ are H;
  $Q^6$ is methyl and $Q^1$, $Q^2$, $Q^3$, $Q^4$, $Q^5$, $Q^7$, and $Q^8$ are H; or
  $Q^8$ is methyl and $Q^1$, $Q^2$, $Q^3$, $Q^4$, $Q^5$, $Q^6$, and $Q^7$ are H.

13. The compound of claim 6, wherein:
  $Q^1$ is —(CO)—$R^5$ and $Q^2$, $Q^3$, $Q^4$, $Q^5$, $Q^6$, $Q^7$, and $Q^8$ are H;
  $Q^2$ and $Q^3$ are —(CO)—$R^5$ and $Q^1$, $Q^4$, $Q^5$, $Q^6$, $Q^7$, and $Q^8$ are H;
  $Q^3$ is —(CO)—$R^5$ and $Q^1$, $Q^2$, $Q^4$, $Q^5$, $Q^6$, $Q^7$, and $Q^8$ are H;
  $Q^4$ is —(CO)—$R^5$ and $Q^1$, $Q^2$, $Q^3$, $Q^5$, $Q^6$, $Q^7$, and $Q^8$ are H;
  $Q^5$ is —(CO)—$R^5$ and $Q^1$, $Q^2$, $Q^3$, $Q^4$, $Q^6$, $Q^7$, and $Q^8$ are H;
  $Q^6$ is —(CO)—$R^5$ and $Q^1$, $Q^2$, $Q^3$, $Q^4$, $Q^5$, $Q^7$, and $Q^8$ are H;
  $Q^6$ is $C_1$–$C_6$ alkyl and $Q^1$, $Q^2$, $Q^3$, $Q^4$, $Q^5$, $Q^7$, and $Q^8$ are H; or $Q^8$ is $C_1$–$C_6$ alkyl and $Q^1$, $Q^2$, $Q^3$, $Q^4$, $Q^5$, $Q^6$, and $Q^7$ are H.

14. The compound of claim 13, wherein:
$Q^1$ is benzoyl and $Q^2$, $Q^3$, $Q^4$, $Q^5$, $Q^6$, $Q^7$, and $Q^8$ are H;
$Q^2$ and $Q^3$ are acetyl and $Q^1$, $Q^4$, $Q^5$, $Q^6$, $Q^7$, and $Q^8$ are H;
$Q^3$ is acetyl and $Q^1$, $Q^2$, $Q^4$, $Q^5$, $Q^6$, $Q^7$, and $Q^8$ are H;
$Q^4$ is acetyl and $Q^1$, $Q^2$, $Q^3$, $Q^5$, $Q^6$, $Q^7$, and $Q^8$ are H;
$Q^5$ is acetyl and $Q^1$, $Q^2$, $Q^3$, $Q^4$, $Q^6$, $Q^7$, and $Q^8$ are H;
$Q^6$ is acetyl and $Q^1$, $Q^2$, $Q^3$, $Q^4$, $Q^5$, $Q^7$, and $Q^8$ are H;
$Q^6$ is methyl and $Q^1$, $Q^2$, $Q^3$, $Q^4$, $Q^5$, $Q^7$, and $Q^8$ are H; or
$Q^8$ is methyl and $Q^1$, $Q^2$, $Q^3$, $Q^4$, $Q^5$, $Q^6$, and $Q^7$ are H.

15. A compound having the structure of formula (III)

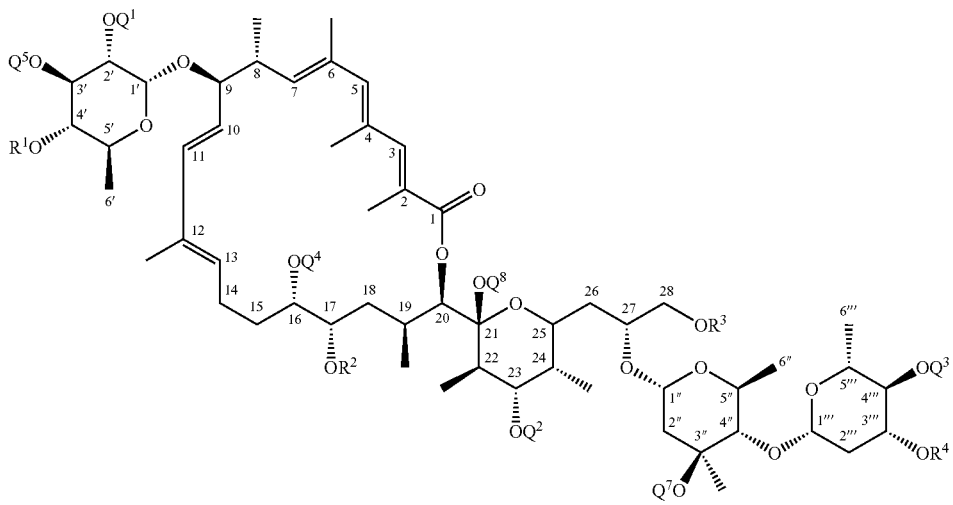

(III)

wherein:
$Q^1$, $Q^2$, $Q^3$, $Q^4$, $Q^5$, $Q^6$, $Q^7$, and $Q^8$ are selected from H, $C_1$–$C_{12}$ hydrocarbyl, acyl of the formula —(CO)—$R^5$ in which $R^5$ is $C_1$–$C_{12}$ hydrocarbyl, and hydroxyl-protecting groups; and
$R^1$, $R^2$, $R^3$, and $R^4$ are $C_1$–$C_{12}$ alkyl or H, with the proviso that at least one of $Q^1$, $Q^2$, $Q^3$, $Q^4$, $Q^5$, $Q^6$, $Q^7$, and $Q^8$ is other than H when $R^1$, $R^2$, $R^3$, and $R^4$ are methyl and the compound has the stereoisomeric configuration of formula (III),
or a stereoisomer thereof.

16. The compound of claim 15, having the stereoisomeric configuration of formula (III).

17. The compound of claim 15, wherein:
$Q^1$, $Q^2$, $Q^3$, $Q^4$, $Q^5$, $Q^6$, $Q^7$, and $Q^8$ are selected from H, $C_1$–$C_6$ hydrocarbyl, —(CO)—$R^5$ wherein $R^5$ is $C_1$–$C_6$ hydrocarbyl, and —Si($R^6R^7R^8$) wherein $R^6$, $R^7$, and $R^8$ are $C_1$–$C_6$ hydrocarbyl; and
$R^1$, $R^2$, $R^3$, and $R^4$ are $C_1$–$C_4$ alkyl.

18. The compound of claim 17, wherein:
$Q^1$, $Q^2$, $Q^3$, $Q^4$, $Q^5$, $Q^6$, $Q^7$, and $Q^8$ are selected from H, $C_1$–$C_6$ alkyl, —(CO)—$R^5$ wherein $R^5$ is $C_1$–$C_6$ alkyl, and —Si($R^6R^7R^8$) wherein $R^6$, $R^7$, and $R^8$ are all methyl or all ethyl; and
$R^1$, $R^2$, $R^3$, and $R^4$ are methyl.

19. The compound of claim 16, wherein:
$Q^1$, $Q^2$, $Q^3$, $Q^4$, $Q^5$, $Q^6$, $Q^7$, and $Q^8$ are selected from H, $C_1$–$C_6$ hydrocarbyl, —(CO)—$R^5$ wherein $R^5$ is $C_1$–$C_6$ hydrocarbyl, and —Si($R^6R^7R^8$) wherein $R^6$, $R^7$, and $R^8$ are $C_1$–$C_6$ hydrocarbyl; and
$R^1$, $R^2$, $R^3$, and $R^4$ are $C_1$–$C_4$ alkyl.

20. The compound of claim 19, wherein:
$Q^1$, $Q^2$, $Q^3$, $Q^4$, $Q^5$, $Q^6$, $Q^7$, and $Q^8$ are selected from H, $C_1$–$C_6$ alkyl, —(CO)—$R^5$ wherein $R^5$ is $C_1$–$C_6$ alkyl, and —Si($R^6R^7R^8$) wherein $R^6$, $R^7$, and $R^8$ are all methyl or all ethyl; and
$R^1$, $R^2$, $R^3$, and $R^4$ are methyl.

21. The compound of claim 15, wherein:
$Q^1$ is —(CO)—$R^5$ and $Q^2$, $Q^3$, $Q^4$, $Q^5$, $Q^6$, $Q^7$, and $Q^8$ are H;
$Q^2$ and $Q^3$ are —(CO)—$R^5$ and $Q^1$, $Q^4$, $Q^5$, $Q^6$, $Q^7$, and $Q^8$ are H;
$Q^3$ is —(CO)—$R^5$ and $Q^1$, $Q^2$, $Q^4$, $Q^5$, $Q^6$, $Q^7$, and $Q^8$ are H;
$Q^4$ is —(CO)—$R^5$ and $Q^1$, $Q^2$, $Q^3$, $Q^5$, $Q^6$, $Q^7$, and $Q^8$ are H;
$Q^5$ is —(CO)—$R^5$ and $Q^1$, $Q^2$ $Q^3$, $Q^4$, $Q^6$, $Q^7$, and $Q^8$ are H;
$Q^6$ is —(CO)—$R^5$ and $Q^1$, $Q^2$, $Q^3$, $Q^4$, $Q^5$, $Q^7$, and $Q^8$ are H;
$Q^6$ is $C_1$–$C_6$ alkyl and $Q^1$, $Q^2$, $Q^3$, $Q^4$, $Q^5$, $Q^7$, and $Q^8$ are H; or
$Q^8$ is $C_1$–$C_6$ alkyl and $Q^1$, $Q^2$, $Q^3$, $Q^4$, $Q^5$, $Q^6$, and $Q^7$ are H.

22. The compound of claim 21, wherein:
$Q^1$ is benzoyl and $Q^2$, $Q^3$, $Q^4$, $Q^5$, $Q^6$, $Q^7$, and $Q^8$ are H;
$Q^2$ and $Q^3$ are acetyl and $Q^1$, $Q^4$, $Q^5$, $Q^6$, $Q^7$, and $Q^8$ are H;
$Q^3$ is acetyl and $Q^1$, $Q^2$, $Q^4$, $Q^5$, $Q^6$, $Q^7$, and $Q^8$ are H;
$Q^4$ is acetyl and $Q^1$, $Q^2$, $Q^3$, $Q^5$, $Q^6$, $Q^7$, and $Q^8$ are H;
$Q^5$ is acetyl and $Q^1$, $Q^2$, $Q^3$, $Q^4$, $Q^6$, $Q^7$, and $Q^8$ are H;
$Q^6$ is acetyl and $Q^1$, $Q^2$, $Q^3$, $Q^4$, $Q^5$, $Q^7$, and $Q^8$ are H;

$Q^6$ is methyl and $Q^1$, $Q^2$, $Q^3$, $Q^4$, $Q^5$, $Q^7$, and $Q^8$ are H; or $Q^8$ is methyl and $Q^1$, $Q^2$, $Q^3$, $Q^4$, $Q^5$, $Q^6$, and $Q^7$ are H.

23. The compound of claim 16, wherein:

$Q^1$ is —(CO)—$R^5$ and $Q^2$, $Q^3$, $Q^4$, $Q^5$, $Q^6$, $Q^7$, and $Q^8$ are H;

$Q^2$ and $Q^3$ are —(CO)—$R^5$ and $Q^1$, $Q^4$, $Q^5$, $Q^6$, $Q^7$, and $Q^8$ are H;

$Q^3$ is —(CO)—$R^5$ and $Q^1$, $Q^2$, $Q^4$, $Q^5$, $Q^6$, $Q^7$, and $Q^8$ are H;

$Q^4$ is —(CO)—$R^5$ and $Q^1$, $Q^2$, $Q^3$, $Q^5$, $Q^6$, $Q^7$, and $Q^8$ are H;

$Q^5$ is —(CO)—$R^5$ and $Q^1$, $Q^2$, $Q^3$, $Q^4$, $Q^6$, $Q^7$, and $Q^8$ are H;

$Q^6$ is —(CO)—$R^5$ and $Q^1$, $Q^2$, $Q^3$, $Q^4$, $Q^5$, $Q^7$, and $Q^8$ are H;

$Q^6$ is $C_1$–$C_6$ alkyl and $Q^1$, $Q^2$, $Q^3$, $Q^4$, $Q^5$, $Q^7$, and $Q^8$ are H; or $Q^8$ is $C_1$–$C_6$ alkyl and $Q^1$, $Q^2$, $Q^3$, $Q^4$, $Q^5$, $Q^6$, and $Q^7$ are H.

24. The compound of claim 23, wherein:

$Q^1$ is benzoyl and $Q^2$, $Q^3$, $Q^4$, $Q^5$, $Q^6$, $Q^7$, and $Q^8$ are H;

$Q^2$ and $Q^3$ are acetyl and $Q^1$, $Q^4$, $Q^5$, $Q^6$, $Q^7$, and $Q^8$ are H;

$Q^3$ is acetyl and $Q^1$, $Q^2$, $Q^4$, $Q^5$, $Q^6$, $Q^7$, and $Q^8$ are H;

$Q^4$ is acetyl and $Q^1$, $Q^2$, $Q^3$, $Q^5$, $Q^6$, $Q^7$, and $Q^8$ are H;

$Q^5$ is acetyl and $Q^1$, $Q^2$, $Q^3$, $Q^4$, $Q^6$, $Q^7$, and $Q^8$ are H;

$Q^6$ is acetyl and $Q^1$, $Q^2$, $Q^3$, $Q^4$, $Q^5$, $Q^7$, and $Q^8$ are H;

$Q^6$ is methyl and $Q^1$, $Q^2$, $Q^3$, $Q^4$, $Q^5$, $Q^7$, and $Q^8$ are H; or $Q^8$ is methyl and $Q^1$, $Q^2$, $Q^3$, $Q^4$, $Q^5$, $Q^6$, and $Q^7$ are H.

25. A compound having the structure of formula (IV)

27. The compound of claim 25, wherein:

$Q^1$, $Q^2$, $Q^4$, $Q^5$, $Q^6$, $Q^8$, and $Q^9$ are independently selected from H, $C_1$–$C_6$ hydrocarbyl, —(CO)—$R^5$ wherein $R^5$ is $C_1$–$C_6$ hydrocarbyl, and —Si($R^6R^7R^8$) wherein $R^6$, $R^7$, and $R^8$ are $C_1$–$C_6$ hydrocarbyl; and $R^1$, $R^2$, and $R^3$ are $C_1$–$C_4$ alkyl.

28. The compound of claim 27, wherein:

$Q^1$, $Q^2$, $Q^4$, $Q^5$, $Q^6$, $Q^8$, and $Q^9$ are independently selected from H, $C_1$–$C_6$ alkyl, —(CO)—$R^5$ wherein $R^5$ is $C_1$–$C_6$ alkyl, and —Si($R^6R^7R^8$) wherein $R^6$, $R^7$, and $R^8$ are all methyl or all ethyl; and $R^1$, $R^2$, and $R^3$ are methyl.

29. The compound of claim 26, wherein:

$Q^1$, $Q^2$, $Q^4$, $Q^5$, $Q^6$, $Q^8$, and $Q^9$ are independently selected from H, $C_1$–$C_6$ hydrocarbyl, —(CO)—$R^5$ wherein $R^5$ is $C_1$–$C_6$ hydrocarbyl, and —Si($R^6R^7R^8$) wherein $R^6$, $R^7$, and $R^8$ are $C_1$–$C_6$ hydrocarbyl; and $R^1$, $R^2$, and $R^3$ are $C_1$–$C_4$ alkyl.

30. The compound of claim 29, wherein:

$Q^1$, $Q^2$, $Q^4$, $Q^5$, $Q^6$, $Q^8$, and $Q^9$ are independently selected from H, $C_1$–$C_6$ alkyl, —(CO)—$R^5$ wherein $R^5$ is $C_1$–$C_6$ alkyl, and —Si($R^6R^7R^8$) wherein $R^6$, $R^7$, and $R^8$ are all methyl or all ethyl; and $R^1$, $R^2$, and $R^3$ are methyl.

31. A functionalized apoptolidin compound consisting essentially of anapoptolidin core in which:

(a) at least one hydroxyl group in the apoptolidin core is replaced with a substituent selected from $C_1$–$C_{24}$ hydrocarbyloxy, $C_2$–$C_{25}$ acyloxy, $C_2$–$C_{25}$ haloacyloxy $C_2$–$C_{25}$ thioacyloxy, $C_2$–$C_{25}$ thiohaloacyloxy, $C_2$–$C_{25}$

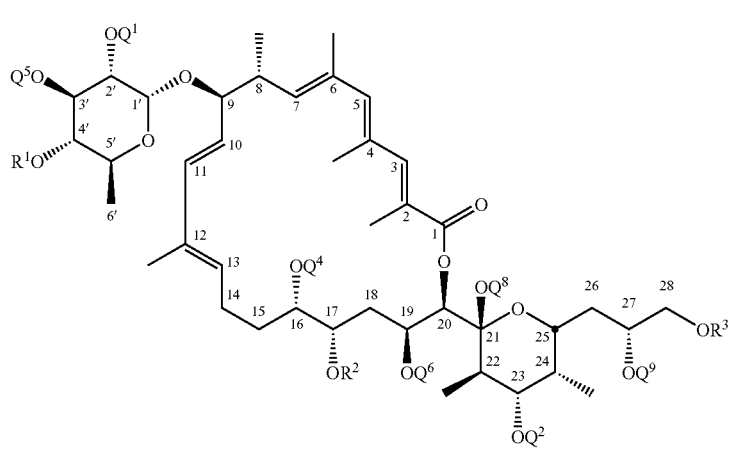

(IV)

wherein:

$Q^1$, $Q^2$, $Q^4$, $Q^5$, $Q^6$, $Q^8$, and $Q^9$ are independently selected from H, $C_1$–$C_{12}$ hydrocarbyl, acyl of the formula —(CO)—$R^5$ in which $R^5$ is $C_1$–$C_{12}$ hydrocarbyl, and hydroxyl-protecting groups; and $R^1$, $R^2$, and $R^3$ are independently selected from $C_1$–$C_{12}$ alkyl and H, or a stereoisomer thereof.

26. The compound of claim 25, having the stereoisomeric configuration of formula (IV).

carbonato, halogenated $C_2$–$C_{25}$ carbonato, $C_2$–$C_{25}$ thiocarbonato, halogenated $C_2$–$C_{25}$ thiocarbonato, carbamoyloxy, N—($C_1$–$C_{24}$ hydrocarbyl)-substituted carbamoyloxy, N,N-di($C_1$–$C_{24}$ hydrocarbyl)-substituted carbamoyloxy, thiocarbamoyloxy, N—($C_1$–$C_{24}$ hydrocarbyl)-substituted thiocarbamoyloxy, N,N-di($C_1$–$C_{24}$ hydrocarbyl)-substituted thiocarbamoyloxy, sulfamoyloxy, N—($C_1$–$C_{24}$ hydrocarbyl)-substituted sulfamoyloxy, N,N-di($C_1$–$C_{24}$ hydrocarbyl)-substituted sulfamoyloxy, and protected hydroxyl groups;

(b) at least one 1,3-diene functionality in the apoptolidin core is replaced by the product of a Diels-Alder reaction with a dienophile;

(c) at least one carbon-carbon double bond in the apoptolidin core is replaced with a carbon-carbon single bond; and/or (d) at least one 1,2-diol functionality in the apoptolidin core is replaced with a cyclic ether.

32. The functionalized apoptolidin compound of claim 31, in which at least one hydroxyl group in the isoapoptolidin core is replaced with a substituent selected from $C_1$–$C_{24}$ hydrocarbyloxy, $C_2$–$C_{25}$ acyloxy, $C_2$–$C_{25}$ haloacyloxy $C_2$–$C_{25}$ thioacyloxy, $C_2$–$C_{25}$ thiohaloacyloxy, $C_2$–$C_{25}$ carbonato, halogenated $C_2$–$C_{25}$ carbonato, $C_2$–$C_{25}$ thiocarbonato, halogenated $C_2$–$C_{25}$ thiocarbonato, carbamoyloxy, N—($C_1$–$C_{24}$ hydrocarbyl)-substituted carbamoyloxy, N,N-di($C_1$–$C_{24}$ hydrocarbyl)-substituted carbamoyloxy, thiocarbamoyloxy, N—($C_1$–$C_{24}$ hydrocarbyl)-substituted thiocarbamoyloxy, N,N-di($C_1$–$C_{24}$ hydrocarbyl)-substituted thiocarbamoyloxy, sulfamoyloxy, N—($C_1$–$C_{24}$ hydrocarbyl)-substituted sulfamoyloxy, N,N-di($C_1$–$C_{24}$ hydrocarbyl)-substituted sulfamoyloxy, and protected hydroxyl groups.

33. The functionalized apoptolidin compound of claim 32, wherein the substituent is selected from $C_1$–$C_{12}$ hydrocarbyloxy, $C_2$–$C_{13}$ acyloxy, $C_2$–$C_{13}$ haloacyloxy $C_2$–$C_{13}$ thioacyloxy, $C_2$–$C_{25}$ thiohaloacyloxy, $C_2$–$C_{13}$ carbonato, halogenated $C_2$–$C_{13}$ carbonato, $C_2$–$C_{13}$ thiocarbonato, halogenated $C_2$–$C_{13}$ thiocarbonato, carbamoyloxy, N—($C_1$–$C_{12}$ hydrocarbyl)-substituted carbamoyloxy, N,N-di($C_1$–$C_{12}$ hydrocarbyl)-substituted carbamoyloxy, thiocarbamoyloxy, N—($C_1$–$C_{12}$ hydrocarbyl)-substituted thiocarbamoyloxy, N,N-di($C_1$–$C_{12}$ hydrocarbyl)-substituted thiocarbamoyloxy, sulfamoyloxy, N—($C_1$–$C_{12}$ hydrocarbyl)-substituted sulfamoyloxy, N,N-di($C_1$–$C_{12}$ hydrocarbyl)-substituted sulfamoyloxy, ($C_1$–$C_6$ alkoxy)methyl ether, ($C_1$–$C_6$ alkylthio) methyl ether, and tri($C_1$–$C_{12}$ hydrocarbyl)-substituted silyloxy.

34. The functionalized apoptolidin compound of claim 33, wherein the substituent is selected from $C_1$–$C_{12}$ hydrocarbyloxy, $C_2$–$C_{13}$ acyloxy, and tri($C_2$–$C_{12}$ hydrocarbyl)-substituted silyloxy.

35. A composition of matter consisting essentially of isoapoptolidin in isolated, purified form.

36. A compound prepared by reaction of the compound of claim 5 with a dienophile, wherein the C-10/C-13 diene functionality is converted to a cyclic group.

37. A compound prepared by reaction of the compound of claim 15 with a dienophile, wherein the C-10/C-13 diene functionality is converted to a cyclic group.

38. A compound prepared by reaction of the compound of claim 25 with a dienophile, wherein the C-10/C-13 diene functionality is converted to a cyclic group.

39. The compound of any one of claims 36, 37, and 38, wherein the dienophile is an N-halosuccinimide.

40. A compound prepared by catalytic hydrogenation of the compound of claim 5, wherein at least one carbon-carbon double bond of the compound of claim 5 is converted to a single bond.

41. A compound prepared by catalytic hydrogenation of the compound of claim 15, wherein at least one carbon-carbon double bond of the compound of claim 15 is converted to a single bond.

n

42. A compound prepared by catalytic hydrogenation of the compound of claim 25, wherein at least one carbon-carbon double bond of the compound of claim 15 is converted to a single bond.

43. A compound prepared by nucleophilic addition of the compound of claim 5, wherein at least one carbon-carbon double bond of the compound of claim 5 is converted to a single bond.

n

44. A compound prepared by nucleophilic addition of the compound of claim 15, wherein at least one carbon-carbon double bond of the compound of claim 15 is converted to single bond.

45. A compound prepared by nucleophilic addition of the compound of claim 25, wherein at least one carbon-carbon double bond of the compound of claim 25 is converted to single bond.

46. The compound of claim 5, wherein at least one 1,2-diol functionality of the compound of claim 5 is converted to a cyclic ether.

47. The compound of claim 15, wherein at least one 1,2-diol functionality of the compound of claim 15 is converted to a cyclic ether.

48. The compound of claim 25, wherein at least one 1,2-diol functionality of the compound of claim 26 is converted to a cyclic ether.

49. A pharmaceutical composition comprising a therapeutically effective amount of the compound of claims 1, 5, 15, 25, or 35 and a pharmaceutically acceptable carrier.

50. The composition of claim 49, wherein the therapeutically effective amount is a unit dosage and the composition is composed of a unit dosage form.

51. The composition of claim 49, comprising a sustained release formulation.

52. A method for inducing apoptosis in cancer cells, wherein the compound of anyone of claims 1, 5, 15, 25, or 35 is administered to the cancer cells.

53. A composition of matter consisting essentially of deglycosylated isoapoptolidin in isolated, purified form.

54. A compound having the structure of formula (V)

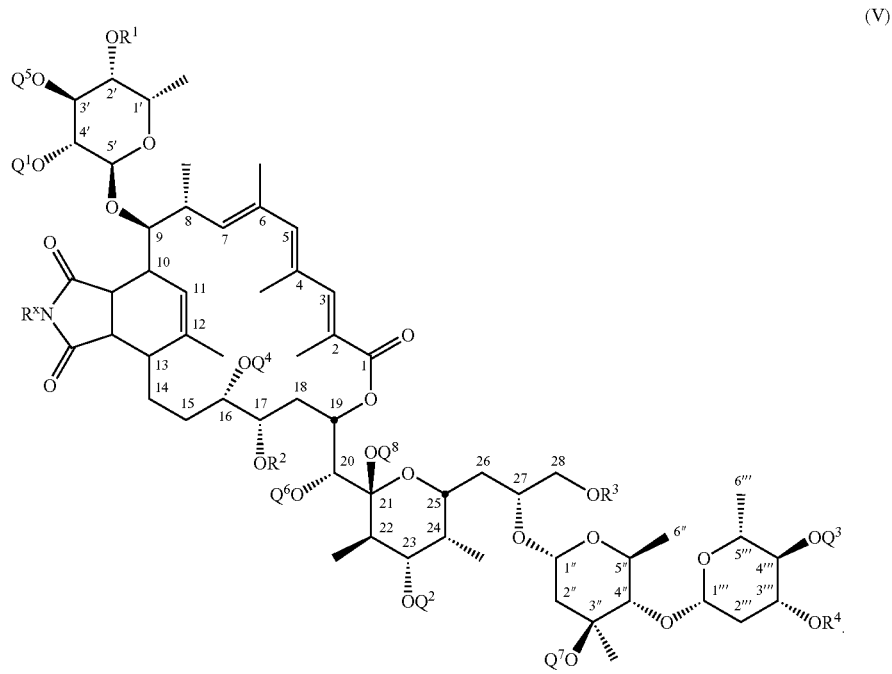

wherein:

$Q^1$, $Q^2$, $Q^3$, $Q^4$, $Q^5$, $Q^6$, $Q^7$, and $Q^8$ are independently selected from H, $C_1$–$C_{12}$ hydrocarbyl, acyl of the formula —(CO)—$R^5$ in which $R^5$ is $C_1$–$C_{12}$ hydrocarbyl, and hydroxyl-protecting groups; and $R^1$, $R^2$, $R^3$, and $R^4$ are $C_1$–$C_{12}$ alkyl or H, or a stereoisomer thereof.

55. The compound of claim 54 oxidatively cleaved at the C-20/C-21 bond.

56. The compound of claim 54 oxidatively cleaved at the C-22/C-23 bond.

* * * * *